US012612665B2

(12) United States Patent
Yang et al.

(10) Patent No.: US 12,612,665 B2
(45) Date of Patent: Apr. 28, 2026

(54) LONG NON-CODING RNA LETN SERVING AS TUMOR MARKER AND THERAPEUTIC TARGET POINT

(71) Applicant: Tsinghua University, Beijing (CN)

(72) Inventors: Xuerui Yang, Beijing (CN); Xianteng Wang, Beijing (CN); Xiaolin Hu, Beijing (CN)

(73) Assignee: Tsinghua University, Beijing (CN)

( * ) Notice: Subject to any disclaimer, the term of this patent is extended or adjusted under 35 U.S.C. 154(b) by 918 days.

(21) Appl. No.: 17/757,289

(22) PCT Filed: Dec. 11, 2019

(86) PCT No.: PCT/CN2019/124579
§ 371 (c)(1),
(2) Date: Jun. 13, 2022

(87) PCT Pub. No.: WO2021/114137
PCT Pub. Date: Jun. 17, 2021

(65) Prior Publication Data
US 2023/0129013 A1     Apr. 27, 2023

(51) Int. Cl.
*C12Q 1/6886* (2018.01)
*G01N 33/50* (2006.01)

(52) U.S. Cl.
CPC ....... *C12Q 1/6886* (2013.01); *G01N 33/5011* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 10,233,495 | B2 | 3/2019 | Hatchwell |
| 11,591,601 | B2 | 2/2023 | Joung |
| 11,667,974 | B2 | 6/2023 | Firat |
| 2013/0178428 | A1 | 7/2013 | Hoon |
| 2015/0329858 | A1 | 11/2015 | Aburatani |
| 2020/0248184 | A1 | 8/2020 | Joung |
| 2021/0189491 | A1 | 6/2021 | Firat |

FOREIGN PATENT DOCUMENTS

| | | |
|---|---|---|
| CN | 104726570 A | 6/2015 |
| CN | 105274111 A | 1/2016 |
| CN | 105316402 A | 2/2016 |
| CN | 105950628 A | 9/2016 |
| CN | 106434868 A | 2/2017 |
| CN | 107022625 A | 8/2017 |
| CN | 107213161 A | 9/2017 |
| CN | 107236817 A | 10/2017 |
| CN | 108384855 A | 8/2018 |
| CN | 108531596 A | 9/2018 |
| CN | 109593848 A | 4/2019 |
| CN | 109722479 A | 5/2019 |
| JP | 2016529246 A | 9/2016 |
| WO | WO2018204777 A2 | 11/2018 |
| WO | WO 2018229046 A1 | 11/2018 |
| WO | WO2018219264 A1 | 12/2018 |
| WO | WO2019095541 A1 | 5/2019 |

OTHER PUBLICATIONS

Zhang et al., Systematic identification of cancer-related long noncoding RNAs and aberrant alternative splicing of quintuple-negative lung adenocarcinoma through RNA-Seq. Lung Cancer (2017), 109: 21-27 (Year: 2017).*
Jiang et al., Emerging roles of lncRNA in cancer and therapeutic opportunities. Am J Cancer Res (2019), 9: 1354-1366 (Year: 2019).*
Mou et al., Identification of long noncoding RNAs biomarkers in patients with hepatitis B virus-associated hepatocellular carcinoma. Cancer Biomarkers (2018), 23: 95-106 (Year: 2018).*
Li et al., Exploring functions of long noncoding RNAs across multiple cancers through co-expression network. Scientific Reports (2017), 7: 754, pp. 1-13 (Year: 2017).*
Jeong et al., Absence of nucleophosmin 1 (NPM1) gene mutations in common solid cancers. APMIS (2007), 115: 341-346 (Year: 2007).*
Dermani et al., The potential role of nucleophosmin (NPM1) in the development of cancer. J Cell Physiol. (2021), 236: 7832-7852 (Year: 2021).*
Gourvest et al., A novel leukemic route of mutant NPM1 through nuclear import of the overexpressed long noncoding RNA LONA. Leukemia (2021), 35: 2784-2798 (Year: 2021).*
Luo et al., Functional characterization of long noncoding RNA Lnc_bc060912 in human lung carcinoma cells. Biochemistry (2015), 54: 2895-2902 (Year: 2015).*
RP11-196G18.22-001 Transcript and sequence, ENST00000564237, Ensembl Archive released Feb. 2014, https://feb2014.archive.ensembl.org/Homo_sapiens/Transcript/Summary?db=core; g=ENSG00000261716;r=1:149816065-149820591; t=ENST00000564237, [retrieved Jul. 22, 2025] (Year: 2014).*
Olivero and Dimitrova, Identification and characterization of functional long noncoding RNAs in cancer. FASEB Journal (2020), 34: 15630-15646 (Year: 2020).*

(Continued)

*Primary Examiner* — Catherine Konopka
(74) *Attorney, Agent, or Firm* — Knobbe, Martens, Olson & Bear, LLP

(57) ABSTRACT

The invention relates to a long non-coding RNA (LETN) useful as a diagnostic and therapeutic target for cancer. In particular, the invention discloses that lncRNA RP11-196G18.22 (LETN) is overexpressed in cancer cells, and such overexpression can promote the proliferation of cancer cells and are associated with short prognostic survival time in cancer patients. Reducing the expression of this lncRNA results in the inhibition of cancer cell growth, and thus inhibiting the expression of this lncRNA represents a new strategy for cancer therapy.

4 Claims, 5 Drawing Sheets
Specification includes a Sequence Listing.

(56)  References Cited

OTHER PUBLICATIONS

Bhatt, Bhumi, et al., "Long non-coding RNA profiling in human skeletalmuscle and their role in Cancer Cachexia." Journal of Cachexia, Sarcopenia and Muscle. Dec. 2013, vol. 8 issue 6, pp. 1043-1043, XP093067438, doi: 10.1002/jcsm.12255.

Huang, R., et al., "Depletion of the lncRNA RP11-567G11.1 inhibits pancreatic cancer progression." Biomed Pharmacother. Apr. 2019; 112:108685. doi: 10.1016/j.biopha.2019.108685. Epub Feb. 23, 2019. PMID: 30802827.

Ronchetti, D., et al., "A compendium of long non-coding RNAs transcriptional fingerprint in multiple myeloma." Sci Rep 8, 6557 (2018). https://doi.org/10.1038/s41598-018-24701-8.

Wu, W., et al., "Tissue-specific Co-expression of Long Non-coding and Coding RNAs Associated with Breast Cancer." Sci Rep 6, 32731 (2016). https://doi.org/10.1038/srep32731.

Zhang L., et at., "Systematic identification of cancer-related long noncoding RNAs and aberrant alternative splicing of quintuple-negative lung adenocarcinoma through RNA-Seq. Lung Cancer." Jul. 2017; 109:21-27. doi: 10.1016/j.lungcan.2017.04.009. Epub Apr. 21, 2017. PMID: 28577945.

Extended European Search Report in European patent application No. 19955708.3 issued Aug. 3, 2023.

Office Action issued Jul. 4, 2023 in Japanese patent application No. 2022-535254.

Huang R, Nie W, Yao K, Chou J. Depletion of the lncRNA RP11-567G11.1 inhibits pancreatic cancer progression. Biomed Pharmacother. Apr. 2019;112:108685. doi: 10.1016/j.biopha.2019. 108685. Epub Feb. 23, 2019. PMID: 30802827.

Tong W, Yang L, Yu Q, Yao J, He A. A new tumor suppressor lncRNA RP11-190D6.2 inhibits the proliferation, migration, and invasion of epithelial ovarian cancer cells. Onco Targets Ther. Feb. 27, 2017;10:1227-1235. doi: 10.2147/OTT.S125185. PMID: 28280357; PMCID: PMC5338983.

Li, S., Li, B., Zheng, Y. et al. Exploring functions of long noncoding RNAs across multiple cancers through co-expression network. Sci Rep 7, 754 (2017). https://doi.org/10.1038/s41598-017-00856-8.

Wang, X., Hu, X., Song, W. et al. Mutual dependency between lncRNA LETN and protein NPM1 in controlling the nucleolar structure and functions sustaining cell proliferation. Cell Res 31, 664-683 (2021). https://doi.org/10.1038/s41422-020-00458-6.

First Office Action issued on Jun. 21, 2021 regarding the corresponding Chinese patent application CN201911265749.8.

Written Opinion of International Search Report issued Jun. 14, 2022 regarding WO 2021/114137 A1.

* cited by examiner

SEQUENCE LISTING

```
<160> NUMBER OF SEQ ID NOS: 73

<210> SEQ ID NO 1
<211> LENGTH: 4527
<212> TYPE: DNA
<213> ORGANISM: human

<400> SEQUENCE: 1
agagttccga ctgaaatttg agaagctctt tgctattcaa gtggatatgt gcagttgaca      60
gtttgagaga tgcatctagg gttcagtaaa gacaacacaa gcctgtcttt agggtctacc     120
tgtgaactgt gaacacagca atgagaatga tggacatcac ctttaagtat ttttctagac     180
tttattactc atgtgtttgt catgaggtgt aacttagtag ttcatagtcc tataatgtat     240
gttattgact aggtagcatt tatttttcta attgtttctg ttatagtgct gccacatgtg     300
tttcccagaa acgcatttta cccacagttc ttagggttgg cctgattagt ttaattgctg     360
tctgaacctg cttcttactg tgattagttc aggaatctag atcaaactca ttggcattta     420
acatttcagg aagtgaactg agtaacaact aactcagcag gggagtgtag tatgctatta     480
tcttttggga aagcagctta tttgctttca agaggcagca ggaggatgga ctgtctttag     540
gtatgaaggc aagaatgatt atagacaata tgcagaggag gacacagtgt gggagaatca     600
gggaactgag ccactcatgg agttcagcca accttggatc cctgctgcac ctttggactt     660
ccagttaagc caatttgtct gacatattta cttataccag tttgaatctt gaaatatttc     720
aggaataata atttcctaga taaaaggaaa gacctttcat gaaaggtctc aagtcaaata     780
gggtcaatta ggacagagtt gctccaatta catatttgga acagatgtcc aaatgttaat     840
acttgactaa ggctaaagac taatattacc atcacaggaa aaatgtccag ggtttttttt     900
cagatgtgaa attttattta aaaattttaa ataaactaaa tcaaaaaatt ttagtagttg     960
tactaatttc ctggggctgt caaagtacca caaactgtat ggcgtaaaac aacacaaagt    1020
tattctttca tggttttaga ggctagaagt ttgaaatcaa cgtgttggta gggccatgct    1080
ctctccaaac ccactagggg aagactcctg tctttcagtg tctggtagcc ccacttgttc    1140
tttggtttct ggcagcataa ctgtaatctc tacctcagtt ttttcatgta tgtctccatg    1200 ttttttttact ttctttcttg agatggagtt tcactcttgt tgcccaggct ggagtgcagt    1260
ggcatgatct tggcttactg caacctctgt gccccgggtt caagcaattt tcctgcctca    1320
gcctcccgag tagctgggat tacaggcatg cgtcagcacg cccggctgat tttgtatttt    1380
tggtagagat ggagtttcat catgttagtc aggctggcct cgaactgacc tcaggtgatc    1440
cacctgcctt ggcctcccaa agtgctggga ttacagatgt gagccactgc acccggctgt    1500
ctccatgtct tcttataagg gtatcagtca tactggatta gggcccaccc taaagacctc    1560
attttaactt gattacctct gtaaagaccc tgtttccaaa gaaggcaaaa ttctaagcaa    1620
```

-continued

```
ctaggggtta gacttcaaca tatctttcgg ggggacacaa ctcaacccat aacagtagtc    1680
aatggctgtg gcaggctaaa tgtggctccc aaatatgtcc atatcctaat ccctacagcc    1740
tgtgaatatt accttatata gccaagagga ttttgcagat gtgattctga gattgagaga    1800
ttatgccaga ttatccaggt aggccccaaa tgtaatcacc acagtcctta taggagaggc    1860
aagaaagtca agtgtagaag gaggcgatag aaggagagag ggatttgaag attaataggc    1920
tgcttgcttt gaagacagag ggaagggacc ataaaccaga aataaacctc tagaagctgg    1980
aaaaggcatg gaaatagacc ctcccttaag gtctctggag ggagtgcagc cttgatttct    2040
accgagtaaa attgattttg tacttcagac ctccaaaact gtaagagaat gactgttgtt    2100
ttaaaaccat tgagtttgta gtaatttgtt gcagcagcca caagaaacta atacaacatc    2160
tatatagaat tttttcaata attggagaaa tttgaatatg gattgcatat taatattact    2220
gaatcagcat taaatttgtt aggtgtaata atgtgattgt agctatttag gagaatatcc    2280
tatttttaag agacatgcca ccatatttag ggagaagtgc caacatattt gcagtttatt    2340
ttcaaatggt tcagaggctg tctgtgtaca tgagaagaca aagataaggc aaatgcagca    2400
aaattgtaat aattggtgaa tccaggtgaa gggactatgg ctggtctttg tacttttttt    2460
tccaactttt ctgtaggttt aaaattttca aaataaaaaa atgggaaata ctttaaaaat    2520
tgtaatcaaa gacattagta cagaaacttt cataatgtat tttattttta cagtaaaatt    2580
aatttatgta aattgataga attttactaa tttcactccc aagttacatt aaaaggctta    2640
catatgtttg ataatagcat atgtaaacta gaactctgaa tgatatccat tggtcataat    2700
acgtactatg tagcggtaat ggtgactttt gtgattgcac aagtctagag atgccccaaa    2760
tgacattgac ttagacatct ggttattcta aggctgaaac tgaagttgaa tagaaggttt    2820
tagtcaaata ctgagatgaa aactgaggca gtcctggcgg gggggagtga gtgtgtgtgt    2880
atatatacac acatagacat catgcttcta aacatttaca gaaagaaagg gtagattatc    2940
tacaaaaaaa taagaatcag actgatatga gatcttacaa acctaacccc cttctctttc    3000
ctaaactcca gattctcata tttctgactt cctatttgat atttacactt cgatatttac    3060
caggagtctt caacattttg ttcaaaacag tactcttggt tttcttcctc caagactact    3120
ccttactcat atcagcaaat agcagctctt ttcaagtgct cagtgtaaaa acctacaatt    3180
aatccttgat ttctctttca gtcagcctat actaaatcaa tttcatttaa aatatctcgg    3240
ctactactct gcatctccac tgctaccatc ggcctctcca gtcacattct ccaagagcac    3300
tctatctcat ttaaaagaca aaatctctgc agtggcctgt gatgctcctt aatggcctac    3360
ataatccagc cctcaagcac ctccgtgatc tctgtaaaac tttcccttgg tcactgtgct    3420
tcagccacat taaccagctt gcatatttct cacattcacc aagcttgttc ctgccttggg    3480
gcctttgtac ttaccatgtt ctgttctgag aatactctgc ctcaagatat cctacaacta    3540
tcttactgta ttcagctctc tgctcaagta ttaactgatg aaacctgtca tccctactcc    3600
actccatgtt ctgctttact taacagcaat tgcacatatg gcccctgaa taatatacat    3660 ttagtcactt attttttactt atctgctaat taaaatgtag actttttcta ttctgtttac    3720
tgctgtattc ccagcatgtt ttatccgaat gtgcagtggt ttcttttctt ctcccttatc    3780
gtgggaagtg atgtgcacaa atacacataa tggagcctga atgtcatatt gctttcatac    3840
ctgtgtgaat tttggtaaga aaggaaaagt agcgattgac aggtaatata attacattaa    3900
gtcactctca tagttagctg tttattgctt tcctgctctt attctcagtc cccaggacca    3960
aatgttgacc actaccttcc cccacatata attaggttat ttaccgaacg ccatgcaggt    4020
```

-continued

```
ggctgttaaa aggaagatat atacttacct tataaactca acttttccct gttgtctttc      4080
tgtctcaccc ctacctccat gctttaaatt aacttttcag gcttaggcct tatctctcag      4140
tagagccata taaggtatgt gtaaaagcag gaaaatgttt cctggggatg aagctttgaa      4200
aagctttttt ttttttttct tttggcaata aaataaggta gattcagcac aatacctaat      4260
aactaaaaaa tctgtttta attgggtggg gcagacagca agtgtgtcat cctggaagat      4320
actatttggg attttatgta ggtacataag agaaaaaagt gaacaaaagc aagggggctac     4380 caggacgccg cagtatgctt aacatgtatt ttctaagttt gtattatgcc tttatcttgg      4440
tacttttatc ttctgttctc acttgatctt tttgaaatgt attttaaatc ctaataaaaa      4500
tatataaagt ctggaattaa taaagga                                          4527
```

```
<210> SEQ ID NO 2
<211> LENGTH: 19
<212> TYPE: RNA
<213> ORGANISM: artificial sequence
<220> FEATURE:
<223> OTHER INFORMATION: siRP11-284F21.10 sense

<400> SEQUENCE: 2
ccaguucucc uaaaugcuu                                                    19
```

```
<210> SEQ ID NO 3
<211> LENGTH: 19
<212> TYPE: RNA
<213> ORGANISM: artificial sequence
<220> FEATURE:
<223> OTHER INFORMATION: siRP11-284F21.10 Antisense

<400> SEQUENCE: 3
aagcauuuag gagaacugg                                                    19
```

```
<210> SEQ ID NO 4
<211> LENGTH: 19
<212> TYPE: RNA
<213> ORGANISM: artificial sequence
<220> FEATURE:
<223> OTHER INFORMATION: siLL22NC03-N14H11.1 Sense

<400> SEQUENCE: 4
gagccuuucc ugcccgcuu                                                    19
```

```
<210> SEQ ID NO 5
<211> LENGTH: 19
<212> TYPE: RNA
<213> ORGANISM: artificial sequence
<220> FEATURE:
<223> OTHER INFORMATION: siLL22NC03-N14H11.1 Antisense

<400> SEQUENCE: 5
aagcgggcag gaaaggcuc                                                    19
```

```
<210> SEQ ID NO 6
<211> LENGTH: 19
<212> TYPE: RNA
<213> ORGANISM: artificial sequence
<220> FEATURE:
<223> OTHER INFORMATION: siLINC00853 Sense

<400> SEQUENCE: 6
gcucucauca aucuacgcu                                                    19
```

-continued

```
<210> SEQ ID NO 7
<211> LENGTH: 19
<212> TYPE: RNA
<213> ORGANISM: artificial sequence
<220> FEATURE:
<223> OTHER INFORMATION: siLINC00853 Antisense

<400> SEQUENCE: 7
agcguagauu gaugagagc                                                     19

<210> SEQ ID NO 8
<211> LENGTH: 19
<212> TYPE: RNA
<213> ORGANISM: artificial sequence
<220> FEATURE:
<223> OTHER INFORMATION: siCTD-2227E11.1 Sense

<400> SEQUENCE: 8
gugucucugg gaagcccuu                                                     19

<210> SEQ ID NO 9
<211> LENGTH: 19
<212> TYPE: RNA
<213> ORGANISM: artificial sequence
<220> FEATURE:
<223> OTHER INFORMATION: siCTD-2227E11.1 Antisense

<400> SEQUENCE: 9
aagggcuucc cagagacac                                                     19

<210> SEQ ID NO 10
<211> LENGTH: 19
<212> TYPE: RNA
<213> ORGANISM: artificial sequence
<220> FEATURE:
<223> OTHER INFORMATION: siAL450992.2 Sense

<400> SEQUENCE: 10
ggagucaugu guuggagau                                                     19

<210> SEQ ID NO 11
<211> LENGTH: 19
<212> TYPE: RNA
<213> ORGANISM: artificial sequence
<220> FEATURE:
<223> OTHER INFORMATION: siAL450992.2 Antisense

<400> SEQUENCE: 11
aucuccaaca caugacucc                                                     19

<210> SEQ ID NO 12
<211> LENGTH: 19
<212> TYPE: RNA
<213> ORGANISM: artificial sequence
<220> FEATURE:
<223> OTHER INFORMATION: siRP11-14N7.2 Sense

<400> SEQUENCE: 12
cuccacauau gaaacccuu                                                     19

<210> SEQ ID NO 13
<211> LENGTH: 19
<212> TYPE: RNA
<213> ORGANISM: artificial sequence
<220> FEATURE:
<223> OTHER INFORMATION: siRP11-14N7.2 Antisense
```

-continued

<400> SEQUENCE: 13
aaggguuuca uauguggag                                                    19

<210> SEQ ID NO 14
<211> LENGTH: 19
<212> TYPE: RNA
<213> ORGANISM: artificial sequence
<220> FEATURE:
<223> OTHER INFORMATION: siLINC00665 Sense

<400> SEQUENCE: 14
cagaugaagg uauaucauu                                                    19

<210> SEQ ID NO 15
<211> LENGTH: 19
<212> TYPE: RNA
<213> ORGANISM: artificial sequence
<220> FEATURE:
<223> OTHER INFORMATION: siLINC00665 Antisense

<400> SEQUENCE: 15
aaugauauac cuucaucug                                                    19

<210> SEQ ID NO 16
<211> LENGTH: 19
<212> TYPE: RNA
<213> ORGANISM: artificial sequence
<220> FEATURE:
<223> OTHER INFORMATION: siRP11-396C23.2 Sense

<400> SEQUENCE: 16
gccgucgccg cagcuccuu                                                    19

<210> SEQ ID NO 17
<211> LENGTH: 19
<212> TYPE: RNA
<213> ORGANISM: artificial sequence
<220> FEATURE:
<223> OTHER INFORMATION: siRP11-396C23.2 Antisense

<400> SEQUENCE: 17
aaggagcugc ggcgacggc                                                    19

<210> SEQ ID NO 18
<211> LENGTH: 19
<212> TYPE: RNA
<213> ORGANISM: artificial sequence
<220> FEATURE:
<223> OTHER INFORMATION: siHCG25 Sense

<400> SEQUENCE: 18
ccacucucag cccucaggaa                                                   19

<210> SEQ ID NO 19
<211> LENGTH: 19
<212> TYPE: RNA
<213> ORGANISM: artificial sequence
<220> FEATURE:
<223> OTHER INFORMATION: siHCG25 Antisense

<400> SEQUENCE: 19
uuccugaggc ugagagugg                                                    19

<210> SEQ ID NO 20

```
<211> LENGTH: 19
<212> TYPE: RNA
<213> ORGANISM: artificial sequence
<220> FEATURE:
<223> OTHER INFORMATION: siDUXAP8 Sense

<400> SEQUENCE: 20
ccugguaagg cuugaaguu                                                          19

<210> SEQ ID NO 21
<211> LENGTH: 19
<212> TYPE: RNA
<213> ORGANISM: artificial sequence
<220> FEATURE:
<223> OTHER INFORMATION: siDUXAP8 Antisense

<400> SEQUENCE: 21
aacuucaagc cuuaccagg                                                          19

<210> SEQ ID NO 22
<211> LENGTH: 19
<212> TYPE: RNA
<213> ORGANISM: artificial sequence
<220> FEATURE:
<223> OTHER INFORMATION: siPCAT6 Sense

<400> SEQUENCE: 22
cuccaauuca augccauca                                                          19

<210> SEQ ID NO 23
<211> LENGTH: 19
<212> TYPE: RNA
<213> ORGANISM: artificial sequence
<220> FEATURE:
<223> OTHER INFORMATION: siPCAT6 Antisense

<400> SEQUENCE: 23
ugauggcauu gaauuggag                                                          19

<210> SEQ ID NO 24
<211> LENGTH: 19
<212> TYPE: RNA
<213> ORGANISM: artificial sequence
<220> FEATURE:
<223> OTHER INFORMATION: siLINC00511 Sense

<400> SEQUENCE: 24
cucccagaau gccaggauu                                                          19

<210> SEQ ID NO 25
<211> LENGTH: 19
<212> TYPE: RNA
<213> ORGANISM: artificial sequence
<220> FEATURE:
<223> OTHER INFORMATION: siLINC00511 Antisense

<400> SEQUENCE: 25
aauccuggca uucugggag                                                          19

<210> SEQ ID NO 26
<211> LENGTH: 19
<212> TYPE: RNA
<213> ORGANISM: artificial sequence
<220> FEATURE:
<223> OTHER INFORMATION: siLINC00152 Sense

<400> SEQUENCE: 26
```

-continued ccgucugcau cccucgaau                                                    19

<210> SEQ ID NO 27
<211> LENGTH: 19
<212> TYPE: RNA
<213> ORGANISM: artificial sequence
<220> FEATURE:
<223> OTHER INFORMATION: siLINC00152 Antisense

<400> SEQUENCE: 27
auucgaggga ugcagacgg                                                    19

<210> SEQ ID NO 28
<211> LENGTH: 19
<212> TYPE: RNA
<213> ORGANISM: artificial sequence
<220> FEATURE:
<223> OTHER INFORMATION: siRP11-196G18.22 Sense

<400> SEQUENCE: 28
gcugucucca ugucuucuu                                                    19

<210> SEQ ID NO 29
<211> LENGTH: 19
<212> TYPE: RNA
<213> ORGANISM: artificial sequence
<220> FEATURE:
<223> OTHER INFORMATION: siRP11-196G18.22 Antisense

<400> SEQUENCE: 29
aagaagacau ggagacagc                                                    19

<210> SEQ ID NO 30
<211> LENGTH: 19
<212> TYPE: RNA
<213> ORGANISM: artificial sequence
<220> FEATURE:
<223> OTHER INFORMATION: siPVT1 Sense

<400> SEQUENCE: 30
ggacuugaga acuguccuu                                                    19

<210> SEQ ID NO 31
<211> LENGTH: 19
<212> TYPE: RNA
<213> ORGANISM: artificial sequence
<220> FEATURE:
<223> OTHER INFORMATION: siPVT1 Antisense

<400> SEQUENCE: 31
aaggacaguu cucaagucc                                                    19

<210> SEQ ID NO 32
<211> LENGTH: 19
<212> TYPE: RNA
<213> ORGANISM: artificial sequence
<220> FEATURE:
<223> OTHER INFORMATION: siCRNDE Sense

<400> SEQUENCE: 32
uguugaaaug aaaaauauu                                                    19

<210> SEQ ID NO 33
<211> LENGTH: 19
<212> TYPE: RNA

```
<213> ORGANISM: artificial sequence
<220> FEATURE:
<223> OTHER INFORMATION: siCRNDE Antisense

<400> SEQUENCE: 33 aauauuuuc auuucaaca                                                    19

<210> SEQ ID NO 34
<211> LENGTH: 19
<212> TYPE: RNA
<213> ORGANISM: artificial sequence
<220> FEATURE:
<223> OTHER INFORMATION: siLETN-1 Sense

<400> SEQUENCE: 34
gcugucucca ugucuucuu                                                   19

<210> SEQ ID NO 35
<211> LENGTH: 19
<212> TYPE: RNA
<213> ORGANISM: artificial sequence
<220> FEATURE:
<223> OTHER INFORMATION: siLETN-1 Antisense

<400> SEQUENCE: 35
aagaagacau ggagacagc                                                   19

<210> SEQ ID NO 36
<211> LENGTH: 19
<212> TYPE: RNA
<213> ORGANISM: artificial sequence
<220> FEATURE:
<223> OTHER INFORMATION: siLETN-2 Sense

<400> SEQUENCE: 36
gcucucugcu caaguauua                                                   19

<210> SEQ ID NO 37
<211> LENGTH: 19
<212> TYPE: RNA
<213> ORGANISM: artificial sequence
<220> FEATURE:
<223> OTHER INFORMATION: siLETN-2 Antisense

<400> SEQUENCE: 37
uaauacuuga gcagagagc                                                   19

<210> SEQ ID NO 38
<211> LENGTH: 19
<212> TYPE: RNA
<213> ORGANISM: artificial sequence
<220> FEATURE:
<223> OTHER INFORMATION: siNC(negative control)Sense

<400> SEQUENCE: 38
acgugacacg uucggagaa                                                   19

<210> SEQ ID NO 39
<211> LENGTH: 19
<212> TYPE: RNA
<213> ORGANISM: artificial sequence
<220> FEATURE:
<223> OTHER INFORMATION: siNC(negative control)Antisense

<400> SEQUENCE: 39
uucuccgaac gugucacgu                                                   19
```

```
<210> SEQ ID NO 40
<211> LENGTH: 21
<212> TYPE: RNA
<213> ORGANISM: artificial sequence
<220> FEATURE:
<223> OTHER INFORMATION: siLMNA Sense

<400> SEQUENCE: 40
aucucauccu gaaguugcuu c                                          21

<210> SEQ ID NO 41
<211> LENGTH: 21
<212> TYPE: RNA
<213> ORGANISM: artificial sequence
<220> FEATURE:
<223> OTHER INFORMATION: siLMNA Antisense

<400> SEQUENCE: 41
gaagcaacuu caggaugaga u                                          21

<210> SEQ ID NO 42
<211> LENGTH: 21
<212> TYPE: DNA
<213> ORGANISM: artificial sequence
<220> FEATURE:
<223> OTHER INFORMATION: LETN-1 forward primer

<400> SEQUENCE: 42
gggtctacct gtgaactgtg a                                          21

<210> SEQ ID NO 43
<211> LENGTH: 20
<212> TYPE: DNA
<213> ORGANISM: artificial sequence
<220> FEATURE:
<223> OTHER INFORMATION: LETN-1 reverse primer

<400> SEQUENCE: 43
ggaaacacat gtggcagcac                                            20

<210> SEQ ID NO 44
<211> LENGTH: 20
<212> TYPE: DNA
<213> ORGANISM: artificial sequence
<220> FEATURE:
<223> OTHER INFORMATION: LETN-2 forward primer

<400> SEQUENCE: 44
tggtttctgg cagcataact                                            20

<210> SEQ ID NO 45
<211> LENGTH: 20
<212> TYPE: DNA
<213> ORGANISM: artificial sequence
<220> FEATURE:
<223> OTHER INFORMATION: LETN-2 reverse primer

<400> SEQUENCE: 45
agcctgggca acaagagtga                                            20

<210> SEQ ID NO 46
<211> LENGTH: 20
<212> TYPE: DNA
<213> ORGANISM: artificial sequence
<220> FEATURE:
```

-continued

<223> OTHER INFORMATION: NPM1-N forward primer

<400> SEQUENCE: 46
ttcggttgtg aactaaaggc                                                    20

<210> SEQ ID NO 47
<211> LENGTH: 20
<212> TYPE: DNA
<213> ORGANISM: artificial sequence
<220> FEATURE:
<223> OTHER INFORMATION: NPM1-N reverse primer

<400> SEQUENCE: 47
caagggaaac cgttggctgt                                                    20

<210> SEQ ID NO 48
<211> LENGTH: 23
<212> TYPE: DNA
<213> ORGANISM: artificial sequence
<220> FEATURE:
<223> OTHER INFORMATION: NPM1-C forward primer

<400> SEQUENCE: 48
tctgtagaag acattaaagc aaa                                                23

<210> SEQ ID NO 49
<211> LENGTH: 21
<212> TYPE: DNA
<213> ORGANISM: artificial sequence
<220> FEATURE:
<223> OTHER INFORMATION: NPM1-C reverse primer

<400> SEQUENCE: 49
aatagcctct tggtcagtca t                                                  21

<210> SEQ ID NO 50
<211> LENGTH: 22
<212> TYPE: DNA
<213> ORGANISM: artificial sequence
<220> FEATURE:
<223> OTHER INFORMATION: Pre-rRNA forward primer

<400> SEQUENCE: 50
gccttctcta gcgatctgag ag                                                 22

<210> SEQ ID NO 51
<211> LENGTH: 20
<212> TYPE: DNA
<213> ORGANISM: artificial sequence
<220> FEATURE:
<223> OTHER INFORMATION: Pre-rRNA reverse primer

<400> SEQUENCE: 51
ccataacgga ggcagagaca                                                    20

<210> SEQ ID NO 52
<211> LENGTH: 20
<212> TYPE: DNA
<213> ORGANISM: artificial sequence
<220> FEATURE:
<223> OTHER INFORMATION: 18S rRNA forward primer

<400> SEQUENCE: 52
tcctttggtc gctcgctcct                                                    20

-continued

```
<210> SEQ ID NO 53
<211> LENGTH: 23
<212> TYPE: DNA
<213> ORGANISM: artificial sequence
<220> FEATURE:
<223> OTHER INFORMATION: 18S rRNA reverse primer

<400> SEQUENCE: 53
gatctgataa atgcacgcat ccc                                             23

<210> SEQ ID NO 54
<211> LENGTH: 16
<212> TYPE: DNA
<213> ORGANISM: artificial sequence
<220> FEATURE:
<223> OTHER INFORMATION: 5.8S rRNA forward primer

<400> SEQUENCE: 54
actcggctcg tgcgtc                                                     16

<210> SEQ ID NO 55
<211> LENGTH: 16
<212> TYPE: DNA
<213> ORGANISM: artificial sequence
<220> FEATURE:
<223> OTHER INFORMATION: 5.8S rRNA reverse primer

<400> SEQUENCE: 55
gcgacgctca gacagg                                                     16

<210> SEQ ID NO 56
<211> LENGTH: 20
<212> TYPE: DNA
<213> ORGANISM: artificial sequence
<220> FEATURE:
<223> OTHER INFORMATION: 28S rRNA forward primer

<400> SEQUENCE: 56
gcgggtaaac ggcgggagta                                                 20

<210> SEQ ID NO 57
<211> LENGTH: 21
<212> TYPE: DNA
<213> ORGANISM: artificial sequence
<220> FEATURE:
<223> OTHER INFORMATION: 28S rRNA reverse primer

<400> SEQUENCE: 57
ttggctgtgg tttcgctgga t                                               21

<210> SEQ ID NO 58
<211> LENGTH: 20
<212> TYPE: DNA
<213> ORGANISM: artificial sequence
<220> FEATURE:
<223> OTHER INFORMATION: GAPDH forward primer

<400> SEQUENCE: 58
ggtcaccagg gctgctttta                                                 20

<210> SEQ ID NO 59
<211> LENGTH: 20
<212> TYPE: DNA
<213> ORGANISM: artificial sequence
<220> FEATURE:
<223> OTHER INFORMATION: GAPDH reverse primer
```

-continued

```
<400> SEQUENCE: 59
ttcccgttct cagccttgac                                              20

<210> SEQ ID NO 60
<211> LENGTH: 20
<212> TYPE: DNA
<213> ORGANISM: artificial sequence
<220> FEATURE:
<223> OTHER INFORMATION: ??-actin forward primer

<400> SEQUENCE: 60
tggacatccg caaagacctg                                             20

<210> SEQ ID NO 61
<211> LENGTH: 20
<212> TYPE: DNA
<213> ORGANISM: artificial sequence
<220> FEATURE:
<223> OTHER INFORMATION: ??-actin reverse primer

<400> SEQUENCE: 61
ccgatccaca cggagtactt                                             20

<210> SEQ ID NO 62
<211> LENGTH: 20
<212> TYPE: DNA
<213> ORGANISM: artificial sequence
<220> FEATURE:
<223> OTHER INFORMATION: MALAT1 forward primer

<400> SEQUENCE: 62
gctctgtggt gtgggattga                                             20

<210> SEQ ID NO 63
<211> LENGTH: 20
<212> TYPE: DNA
<213> ORGANISM: artificial sequence
<220> FEATURE:
<223> OTHER INFORMATION: MALAT1 reverse primer

<400> SEQUENCE: 63
gtggcaaaat ggcggacttt                                             20

<210> SEQ ID NO 64
<211> LENGTH: 21
<212> TYPE: DNA
<213> ORGANISM: artificial sequence
<220> FEATURE:
<223> OTHER INFORMATION: shLETN-1 Sense

<400> SEQUENCE: 64
ggacttccag ttaagccaat t                                           21

<210> SEQ ID NO 65
<211> LENGTH: 21
<212> TYPE: DNA
<213> ORGANISM: artificial sequence
<220> FEATURE:
<223> OTHER INFORMATION: shLETN-1 Antisense

<400> SEQUENCE: 65
aattggctta actggaagtc c                                           21

<210> SEQ ID NO 66
<211> LENGTH: 21
```

```
<212> TYPE: DNA
<213> ORGANISM: artificial sequence
<220> FEATURE:
<223> OTHER INFORMATION: shLETN-2 Sense

<400> SEQUENCE: 66
ggctgtctcc atgtcttctt a                                                    21

<210> SEQ ID NO 67
<211> LENGTH: 21
<212> TYPE: DNA
<213> ORGANISM: artificial sequence
<220> FEATURE:
<223> OTHER INFORMATION: shLETN-2 Antisense

<400> SEQUENCE: 67
taagaagaca tggagacagc c                                                    21

<210> SEQ ID NO 68
<211> LENGTH: 20
<212> TYPE: DNA
<213> ORGANISM: artificial sequence
<220> FEATURE:
<223> OTHER INFORMATION: shNC Sense

<400> SEQUENCE: 68
acgtgacacg ttcggagaaa                                                      20

<210> SEQ ID NO 69
<211> LENGTH: 20
<212> TYPE: DNA
<213> ORGANISM: artificial sequence
<220> FEATURE:
<223> OTHER INFORMATION: shNC Antisense

<400> SEQUENCE: 69
tttctccgaa cgtgtcacgt                                                      20

<210> SEQ ID NO 70
<211> LENGTH: 20
<212> TYPE: DNA
<213> ORGANISM: artificial sequence
<220> FEATURE:
<223> OTHER INFORMATION: sgLETN-1 Sense

<400> SEQUENCE: 70
tcaaatttca gtcggaactc                                                      20

<210> SEQ ID NO 71
<211> LENGTH: 20
<212> TYPE: DNA
<213> ORGANISM: artificial sequence
<220> FEATURE:
<223> OTHER INFORMATION: sgLETN-2 Sense

<400> SEQUENCE: 71
gagacgatat gctacgggtg                                                      20

<210> SEQ ID NO 72
<211> LENGTH: 20
<212> TYPE: DNA
<213> ORGANISM: artificial sequence
<220> FEATURE:
<223> OTHER INFORMATION: sgEV-1 Sense

<400> SEQUENCE: 72
```

-continued

```
gaacgttggc actacttcac                                          20

<210> SEQ ID NO 73
<211> LENGTH: 20
<212> TYPE: DNA
<213> ORGANISM: artificial sequence
<220> FEATURE:
<223> OTHER INFORMATION: sgEV-2 Sense

<400> SEQUENCE: 73
gcgccttaag agtactcatc                                          20
```

LONG NON-CODING RNA LETN SERVING AS TUMOR MARKER AND THERAPEUTIC TARGET POINT

TECHNICAL FIELD

The invention relates to the field of cancer. More specifically, the invention relates to the use of long non-coding RNA LETN as a tumor marker and a therapeutic target.

REFERENCE TO ELECTRONIC SEQUENCE LISTING

The present application is filed along with an Electronic Sequence Listing. The Electronic Sequence Listing is provided as a file entitled 55763764_1.txt which is approximately 19.2 kilobytes in size, created on Jun. 9, 2022. The information in the Electronic Sequence Listing is incorporated herein by reference in its entirety.

BACKGROUND

In recent years, with the rapid development of sequencing technology, studies have found that long non-coding RNAs (lncRNAs) without translation activity will be transcribed in a large number of non-coding regions in the human genome, far more than proteins in number. Hundreds of lncRNAs related to various diseases or physiological functions in humans have been discovered. Especially in cancers, there is increasing evidence that lncRNAs play a synergistic role in tumor suppression or tumorigenesis[1]. However, for the vast majority of lncRNAs, we know little about their molecular and biological functions.

Liver hepatocellular carcinoma is the sixth most common cancer in the world and ranks fifth in the cancer incidence worldwide, with approximately 841,000 new cases and 782,000 deaths each year[2], wherein the morbidity and mortality are 2 to 3 times higher in men, ranking second among the deaths in men. China is a high-risk country for liver hepatocellular carcinoma, which is mainly caused by chronic HBV infection and aflatoxin exposure. However, despite the increasing incidence of liver hepatocellular carcinoma, it is surprising that few treatments are available. Apart from physical therapies such as radiation, transplantation, and surgery, there is only one approved drug for advanced hepatocellular carcinoma, namely sorafenib, while it is very expensive and only prolongs life by an average of 2.8 months, and causes various side effects such as diarrhea and nausea[3].

The nucleolus is a non-membrane subnuclear compartment located in the nucleus, which is a crucial organelle for fundamental processes such as rDNA transcription and ribosome biogenesis. NPM1 (also known as B23) is an abundantly expressed protein in the nucleolus, and its protein sequence contains three distinct domains, wherein the N-terminal domain can affect its biological functions by regulating NPM1 oligomerization and the interaction with other proteins. Numerous studies have shown that NPM1 exerts the corresponding functions by forming pentamers. The middle region of NPM1 is an intrinsically disordered region marked by the presence of highly acidic regions and is involved in the binding to histones. The C-terminal region provides a sufficient platform to enable binding to nucleic acids[4]. NPM1, as an important cellular protein, has been shown to be involved in a series of biological processes such as ribosome biogenesis, chromatin remodeling and centriole duplication. Its abnormal expression or mutation will cause abnormal embryonic development and tumorigenesis.

SUMMARY

By combining theoretical research and experimental means, the inventors have conducted a comprehensive analysis and exploration of lncRNAs that may have potential functions in the context of cancer, through multi-omics data mining tools. For the liver hepatocellular carcinoma (LIHC), the inventors have investigated lncRNA functions using the data of the Cancer Genome Atlas (TCGA) through an algorithm designed in the laboratory, and found previously unstudied lncRNA RP11-196G18.22 (designated as LETN). It is predicted to regulate 191 pairs of transcription factors and target genes, and may have extensive and powerful regulatory potentials in the carcinogenesis and progress of liver hepatocellular carcinoma, which is verified by experiments.

Accordingly, the invention relates to a long non-coding RNA (lncRNA RP11-196G18.22, designated herein as LETN) useful as a diagnostic and therapeutic target for cancer. This RNA is overexpressed in cancer cells, and such overexpression can promote the proliferation of cancer cells and are associated with short prognostic survival time in cancer patients, thus serving as a tumor marker and a diagnostic marker. Reducing the expression of this lncRNA results in the inhibition of cancer cell growth, and thus the inhibition of the expression of this lncRNA represents a new strategy for cancer therapy. In present invention, the mechanism of action of LETN is also studied, and it is found that LETN functions by binding to NPM1, and affects the production of rRNA and the assembly function of nucleosome by binding to NPM1 so as to promote the carcinogenesis and progress of cancers (such as liver hepatocellular carcinoma).

According to one aspect of the invention, there is provided the use of an agent for detecting the expression level of lncRNA RP11-196G18.22 (LETN) in the manufacture of a diagnostic agent or a diagnostic kit for cancer. Detecting the expression level of RP11-196G18.22 (LETN) may refer to the detection of DNA or RNA level thereof.

In one embodiment, the invention provides a method of diagnosing cancer, comprising detecting the expression level of lncRNA RP11-196G18.22 (LETN) in a sample from a subject, wherein relative to a control (healthy or normal sample), the overexpression of LETN in the subject's sample is indicative of the subject suffering from a (high) risk of cancer or suffering from cancer.

In one embodiment, the invention provides an agent for detecting the expression level of lncRNA RP11-196G18.22 (LETN), for use in diagnosing cancer.

In one embodiment, the agent is a specific probe, gene chip, or PCR primer for lncRNA RP11-196G18.22.

In another embodiment, the cancer is a solid tumor, preferably selected from the group consisting of liver hepatocellular carcinoma, lung cancer, prostate cancer, breast cancer, prostate cancer, pancreatic cancer, kidney cancer, gastric cancer, soft tissue cancer, biliary cancer, bladder cancer, rectal cancer, endometrial cancer, head and neck cancer, colon cancer, esophageal cancer, and thyroid cancer.

In another preferred embodiment, the lncRNA RP11-196G18.22 has a nucleotide sequence as shown in SEQ ID NO: 1 (Ensembl accession number: ENST00000564237.1).

According to another aspect of the invention, there is provided the use of an agent for reducing or inhibiting the expression of lncRNA RP11-196G18.22 (LETN) in the manufacture of a medicament for treating cancer.

In one embodiment, the invention provides an agent for reducing or inhibiting the expression of lncRNA RP11-196G18.22 (LETN), for use as a medicament, particularly as a medicament for treating cancer.

In another embodiment, the invention provides a method of treating cancer comprising administrating to a subject in need thereof an effective amount of an agent for reducing or inhibiting the expression of lncRNA RP11-196G18.22 (LETN).

The nature of the agent for reducing or inhibiting the expression of lncRNA RP11-196G18.22 (LETN) is not critical to the invention, as long as it reduces or inhibits the expression of lncRNA RP11-196G18.22 (LETN).

According to a preferred embodiment, the agent for reducing or inhibiting the expression of lncRNA RP11-196G18.22 (LETN) is selected from the group consisting of gapmer, antisense RNA, siRNA, esiRNA, shRNA, miRNA, RNA aptamer, TALEN® (Transcription activator-like effector nuclease), CRISPR, and zinc finger nuclease. In particularly preferred embodiments, the specific sequences for antisense RNA, siRNA, shRNA, and CRISPR are those used in Examples in the Description of the subject application.

In another embodiment, the cancer is a solid tumor, preferably selected from the group consisting of liver hepatocellular carcinoma, lung cancer, prostate cancer, breast cancer, prostate cancer, pancreatic cancer, kidney cancer, gastric cancer, soft tissue cancer, biliary cancer, bladder cancer, rectal cancer, endometrial cancer, head and neck cancer, colon cancer, esophageal cancer, and thyroid cancer.

According to a preferred embodiment, the lncRNA RP11-196G18.22 has a nucleotide sequence as shown in SEQ ID NO: 1 (Ensembl accession number: ENST00000564237.1).

In another embodiment, the medicament further comprises an additional anticancer agent such as chemotherapeutic agent, for example, an agent for reducing or inhibiting the expression or mutation of NPM1 or an agent for inhibiting the binding of LETN to NPM1. Alternatively, the medicament is used in combination with a method for reducing or inhibiting the expression or mutation of NPM1, or a method for inhibiting the binding of LETN to NPM1. Even though the inhibition of lncRNA RP11-196G18.22 (LETN) is sufficient for achieving the effect of cancer treatment, it is expected that when combined with other anticancer drugs such as chemotherapeutic agents, the agent for reducing or inhibiting the expression of lncRNA RP11-196G18.22 (LETN) can achieve stronger and even synergistic anticancer effects. Since the invention has found that LETN functions by binding to NPM1 and affects the production of rRNA and the assembly function of nucleosome by binding to NPM1 so as to promote the carcinogenesis and progress of cancer (such as liver hepatocellular carcinoma), this is especially true for the anticancer drug or chemotherapeutic agent for reducing or inhibiting the expression or mutation of NPM1.

According to another aspect of the invention, there is provided a method for screening anticancer drugs, comprising the following steps:

1) determining the expression level of lncRNA RP11-196G18.22 (LETN) in cells overexpressing lncRNA RP11-196G18.22 (LETN);

2) contacting a candidate compound with the cells of step 1);

3) determining the expression level of lncRNA RP11-196G18.22 (LETN) in cells after step 2); and 4) comparing the expression levels of lncRNA RP11-196G18.22 (LETN) determined in step 1) and step 3), wherein a reduced expression level of lncRNA RP11-196G18.22 (LETN) is indicative of the candidate compound having anticancer potential. Preferably, the cells are cancer cells.

According to another aspect of the invention, there is provided a method of identifying whether a tumor is susceptible to treatment with an inhibitor of LETN expression, comprising the following steps:

1) determining whether the expression of LETN in a tumor or tumor cell sample is increased relative to a control (normal or healthy tissue/cell);

2) determining whether the tumor is susceptible to treatment, wherein the increased expression is indicative of being susceptible to treatment with an inhibitor of LETN expression.

According to another aspect of the invention, there is provided a method of evaluating the effect of an agent in the treatment and/or prevention of cancer, wherein the method includes testing whether the agent can reduce the expression of LETN in a tumor or tumor cell sample, and if so, the agent is suitable for the treatment and/or prevention of cancer. In a preferred embodiment, the cancer is a solid tumor, preferably selected from the group consisting of liver hepatocellular carcinoma, lung cancer, prostate cancer, breast cancer, prostate cancer, pancreatic cancer, kidney cancer, gastric cancer, soft tissue cancer, biliary cancer, bladder cancer, rectal cancer, endometrial cancer, head and neck cancer, colon cancer, esophageal cancer, and thyroid cancer. According to a preferred embodiment, LETN has a nucleotide sequence as shown in SEQ ID NO: 1 (Ensembl accession number: ENST00000564237.1).

DESCRIPTION OF THE DRAWINGS

The above-mentioned features and advantages of the invention will become more apparent from the detailed descriptions below in conjunction with the accompanying drawings, wherein.

A shows the expression status of LETN in various cancers and related paracancerous tissues in the TCGA database (CHOL: biliary cancer; LIHC: liver hepatocellular carcinoma; LUAD: lung adenocarcinoma; KIRC: renal clear cell carcinoma; BLCA: bladder cancer; BRCA: breast cancer; PRAD: prostate cancer; READ: rectal cancer; LUSC: lung squamous cell carcinoma; UCEC: endometrial cancer; PAAD: pancreatic cancer; HNSC: head and neck squamous cancer; KIRP: papillary renal cell carcinoma; COAD: colon cancer; STAD: gastric cancer; SARC: soft tissue cancer; ESCA: esophageal cancer; THCA: thyroid cancer; THYM: thymic cancer; KICH: renal chromophobe cell carcinoma; PCPG: adrenal carcinoma; CESC: cervical squamous cell carcinoma), and it is observed that the expression of LETN in most cancer tissues (solid tumors) in humans is higher than that in the corresponding paracancerous tissues; B shows the CRISPR-Cas9 knockout of LETN in the HUH7 cell line, and it is observed that the proliferation rate of cells in the LETN knockout group (sgLETN) is much lower than the control (sgEV); C shows the knockdown of LETN in liver hepatocellular carcinoma cell lines HUH7 and SMMC-7721, lung cancer cell line HCC827, and prostate cancer cell lines PC3 and DU145, respectively; and it is detected that the proliferation rate of cells in the LETN knockdown group is much lower than that of cells in the control group (siNC and siLMNA are two different negative controls; to prevent off-target effects, two siRNAs are designed for LETN knockdown: siLETN-1 and siLETN-2); D and E show that after the stable knockdown/knockout of LETN in HUH7 and HCC827 cells, the colony formation ability of cells is significantly destroyed; F shows the overexpression of LETN in liver hepatocellular carcinoma cell lines HUH7 and SMMC-7721, and it is detected that the proliferation rate of cells in the LETN overexpression group is much higher than that of cells in the control group; G shows that after the stable overexpression of LETN in HUH7 and SMMC-7721 cells, the colony formation ability of cells is significantly enhanced; H shows that after the stable knockdown of LETN in the liver hepatocellular carcinoma cell line HUH7, it is observed that the subcutaneous tumorigenic ability of the LETN knockdown group is significantly reduced; I showed that after the stable overexpression of LETN in the liver hepatocellular carcinoma cell line HUH7, it is observed that the subcutaneous tumorigenic ability of the LETN overexpression group is significantly enhanced (LETN-OE group is the LETN overexpression group, and EV group is the control group).

Figure 2:
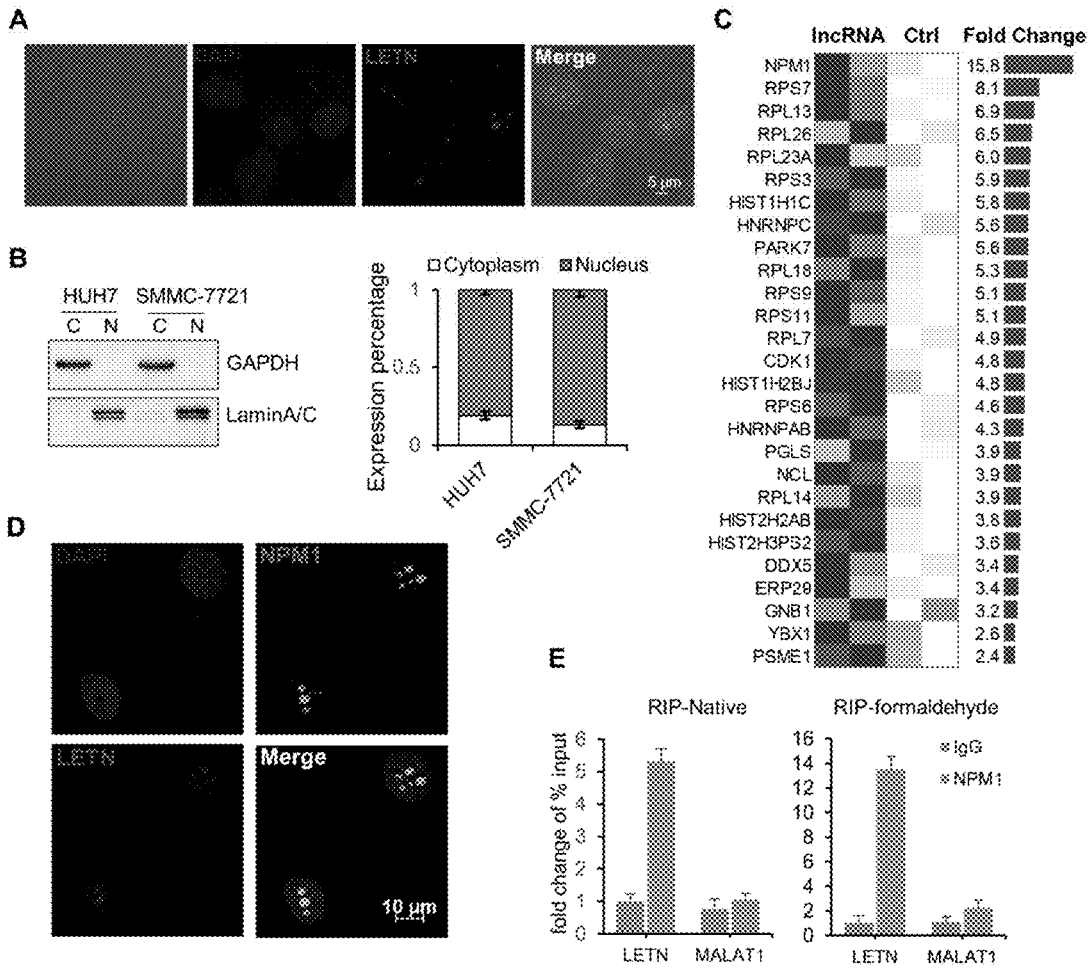

FIG. 2 The results shown in A to E in FIG. 2 demonstrate that LETN functions by binding to NPM1.

Specifically, A shows that it is found in the in situ hybridization experiment that LETN is mainly located in the nucleus and appears in clusters; B shows that it is demonstrated in the nucleocytoplasmic separation experiment that most of LETN is located in the nucleus, and GAPDH and LaminA/C are markers for cytoplasm and nucleus, respectively; C shows that through the mass spectrometry analysis of proteins interacted with LETN, it is found that NPM1 is the protein with the strongest binding ability in both experiments; D shows that it is further confirmed by the cellular fluorescence co-localization experiment that LETN binds to NPM1 and is localized in the nucleolus; E shows the pull down of RNA by NPM1 in the formaldehyde crosslinked or uncrosslinked state, and it is also found that NPM1 can indeed pull down the lncRNA LETN (MALAT1 in the figure represents the negative control).

Figure 3:
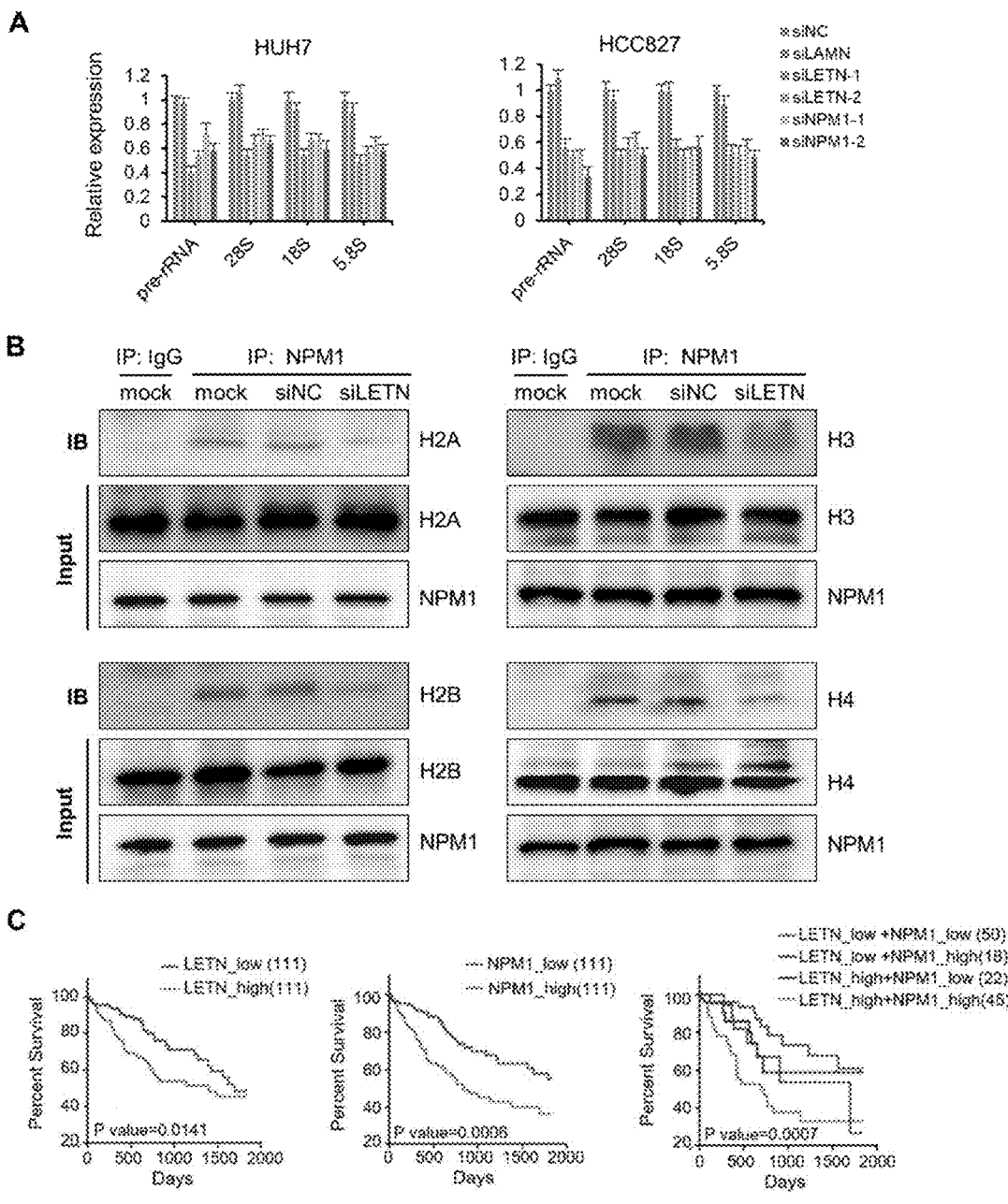

FIG. 3 The results shown in A to C in FIG. 3 demonstrate that LETN promotes the carcinogenesis and progress of liver hepatocellular carcinoma by affecting the production of rRNA and the assembly function of nucleosome via binding to NPM1 (antibodies for detection: mouse anti-human NPM1 antibody (ab10530, abcam), Histone H2A (EPR17470, ab177308, abcam), Histone H2B (EP957Y, ab52599, abeam), Histone H3 (17168-1-AP, proteintech), Histone H4 (16047-1-AP, proteintech)).

Specifically, A shows that the respective knockdown of LETN or NPM1 in HUH7 and HCC827 cell lines can significantly reduce the expressions of various rRNAs, and the functions of LETN and NPM1 are consistent; B shows that the knockdown of LETN can attenuate the binding ability of NPM1 to histones, thereby affecting the assembly of nucleosome; C shows the survival time analysis of the clinical data of liver hepatocellular carcinoma patients in the TCGA database, wherein the prognostic survival time of patients individually divided in LETN or NPM1 high expression group is shorter than that of patients in low expression group; and when further subdivided into four groups: NPM1-low+LETN-low, NPM1-low+LETN-high, NPM1-high+LETN-low, and NPM1-high+LETN-high, it is found that the survival time of patients with high expressions of both NPM1 and LETN is much shorter than that of patients with low expressions of both NPM1 and LETN.

Figure 4:
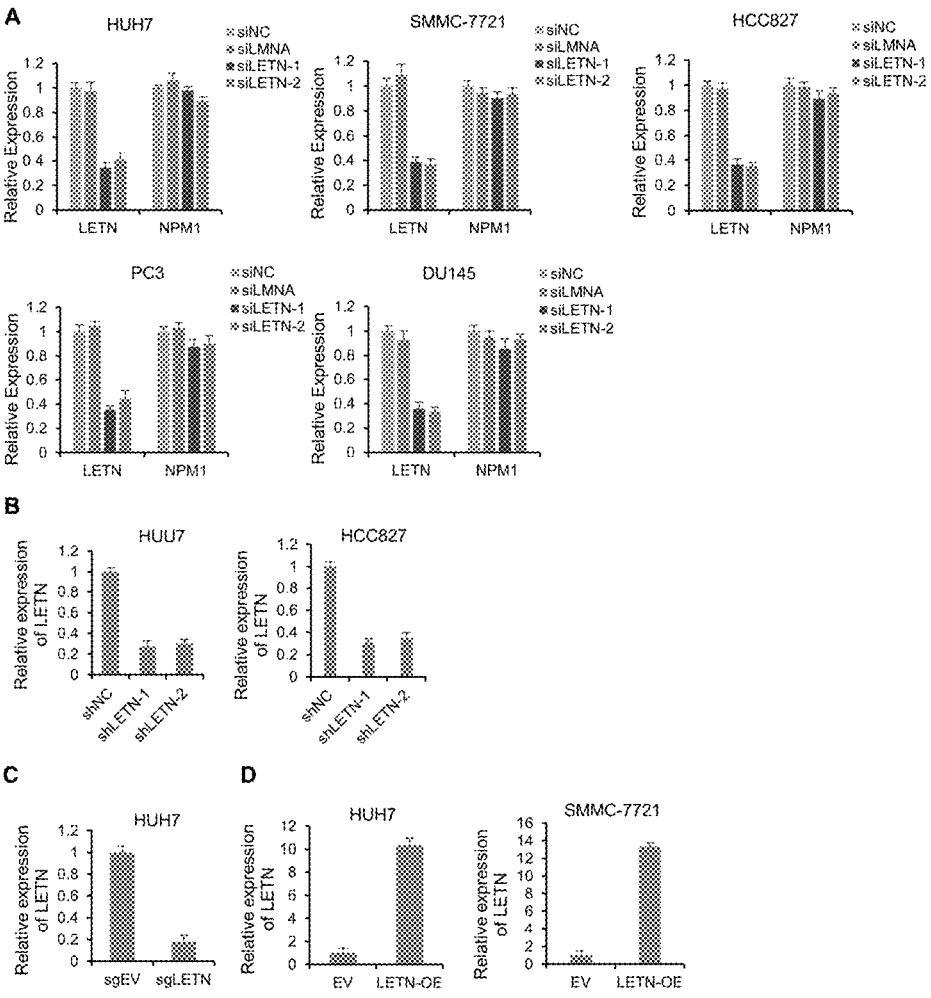

FIG. 4 The results shown in A to D in FIG. 4 demonstrate various knockdown and overexpression efficiencies of LETN.

A shows the knockdown of LETN by siRNA in five cell lines, wherein the knockdown efficiency is detected by RT-qPCR; B shows the knockdown of LETN by lentiviral shRNA in two cell lines, wherein the knockdown efficiency is detected by RT-qPCR; C shows the knockout of LETN by CRISPR-Cas9 technology, wherein the knockdown efficiency is detected by RT-qPCR; D shows the overexpression of LETN by the lentiviral overexpression system in two cell lines, wherein the overexpression efficiency is detected by RT-qPCR.

Figure 5:
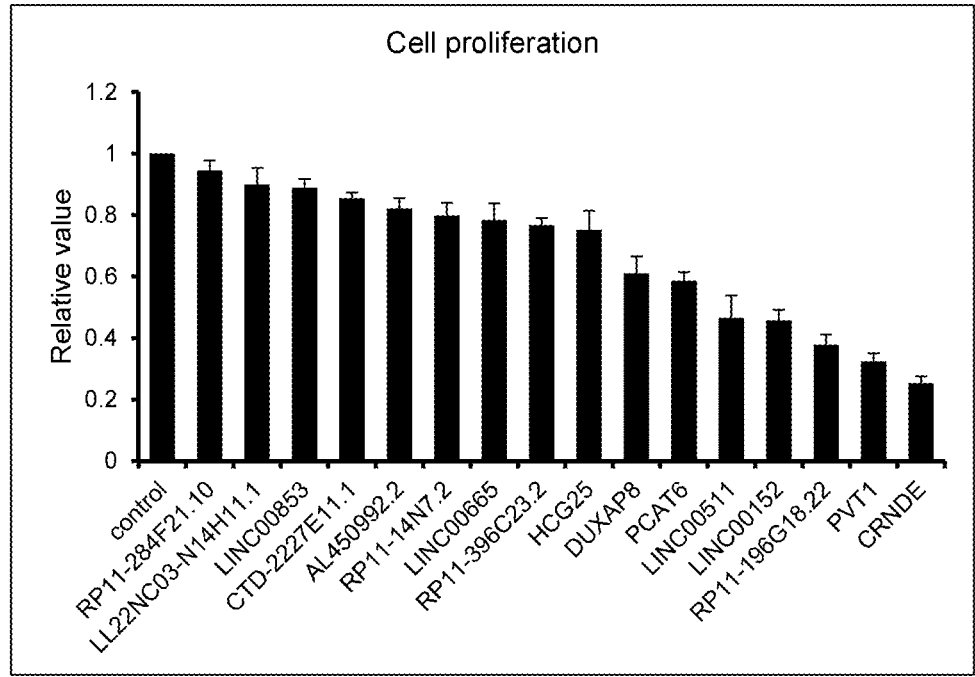

FIG. 5 shows the effect of knockdown of the corresponding lncRNA on the proliferation of liver hepatocellular carcinoma cell line HUH7.

DESCRIPTION OF EMBODIMENTS

Unless otherwise indicated, the terms used herein have ordinary technical meanings as understood by those skilled in the art. For definitions and terms in the art, the skilled artisan is specifically referred to Sambrook et al., Molecular Cloning: A Laboratory Manual, 2nd Edition, Cold Spring Harbor Press, Plainsview, New York (1989); and Ausubel et al., Current Protocols in Molecular Biology (Supplement 47), John Wiley & Sons, New York (1999).

The term "long non-coding RNA" (abbreviated as lncRNA) refers to the transcripts longer than 200 nucleotides that do not encode proteins.

The term "lncRNA RP11-196G18.22" or "LETN" refers to the gene with Ensembl accession number: ENST00000564237.1 and mRNAs transcribed from this gene. Since it is a non-protein-coding gene, there is no protein product. In present invention, its sequence can be represented by SEQ ID NO: 1 (shown below). The invention also contemplates variations in the non-coding exons that may exist in the above-mentioned gene, which variations are considered to belong to the corresponding transcripts; that is, unless otherwise specified, the term "lncRNA RP11-196G18.22" or "LETN" encompasses different isotypes.

(SEQ ID NO: 1)
AGAGTTCCGACTGAAATTTGAGAAGCTCTTTGCTATTCAAGTGGATATGT

GCAGTTGACAGTTTGAGAGATGCATCTAGGGTTCAGTAAAGACAACACAA

GCCTGTCTTTAGGGTCTACCTGTGAACTGTGAACACAGCAATGAGAATGA

TGGACATCACCTTTAAGTATTTTTCTAGACTTTATTACTCATGTGTTTGT

CATGAGGTGTAACTTAGTAGTTCATAGTCCTATAATGTATGTTATTGACT

AGGTAGCATTTATTTTTCTAATTGTTTCTGTTATAGTGCTGCCACATGTG

TTTCCCAGAAACGCATTTTACCCACAGTTCTTAGGGTTGGCCTGATTAGT

TTAATTGCTGTCTGAACCTGCTTCTTACTGTGATTAGTTCAGGAATCTAG

ATCAAACTCATTGGCATTTAACATTTCAGGAAGTGAACTGAGTAACAACT

AACTCAGCAGGGGAGTGTAGTATGCTATTATCTTTTGGGAAAGCAGCTTA

TTTGCTTTCAAGAGGCAGCAGGAGGATGGACTGTCTTTAATGGAGTTCAG

GTATGAAGGCAAGAATGATTATAGACAATATGCAGAGGAGGACACAGTGT

GGGAGAATCAGGGAACTGAGCCACTCGCCAACCTTGGATCCCTGCTGCAC

CTTTGGACTTCCAGTTAAGCCAATTTGTCTGACATATTTACTTATACCAG

-continued

TTTGAATCTTGAAATATTTCAGGAATAATAATTTCCTAGATAAAAGGAAA

GACCTTTCATGAAAGGTCTCAAGTCAAATAGGGTCAATTAGGACAGAGTT

GCTCCAATTACATATTTGGAACAGATGTCCAAATGTTAATACTTGACTAA

GGCTAAAGACTAATATTACCATCACAGGAAAAATGTCCAGGGTTTTTTTT

CAGATGTGAAATTTTATTTAAAAATTTTAAATAAACTAAATCAAAAAATT

TTAGTAGTTGTACTAATTTCCTGGGGCTGTCAAAGTACCACAAACTGTAT

GGCGTAAAACAACACAAAGTTATTCTTTCATGGTTTTAGAGGCTAGAAGT

GTTGAAATCAACGTGTTGGTAGGGCCATCTCTCTCCAAACCCACTAGGGG

AAGACTCCTGTCTTTCAGTGTCTGGTAGCCCCACTTGTTCTTTGGTTTCT

GGCAGCATAACTGTAATCTCTACCTCAGTTTTTTCATGTATGTCTCCATG

TTTTTTTACTTTCTTTCTTGAGATGGAGTTTCACTCTTGTTGCCCAGGCT

GGGAGTGCAGTGGCATGATCTTGGCTTACTGCAACCTCTGTGCCCCGGGTT

CAAGCAATTTTCCTGCCTCAGCCTCCCGAGTAGCTGGGATTACAGGCATG

CGTCAGCACGCCCGGCTGATTTTGTATTTTTGGTAGAGATGGAGTTTCAT

CATGTTAGTCAGGCTGGCCTCGAACTGACCTCAGGTGATCCACCTGCCTT

GGCCTCCCAAAGTGCTGGGATTACAGATGTGAGCCACTGCACCCGGCTGT

CTCCATGTCTTCTTATAAGGGTATCAGTCATACTGGATTAGGGCCCACCC

TAAAGACCTCATTTTAACTTGATTACCTCTGTAAAGACCCTGTTTCCAAA

GAAGGCAAAATTCTAAGCAACTAGGGGTTAGACTTCAACATATCTTTCGG

GGGGACACAACTCAACCCATAACAGTAGTCAATGGCTGTGGCAGGCTAAA

TGTGGCTCCCAAATATGTCCATATCCTAATCCCTACAGCCTGTGAATATT

ACCTTATATAGCCAAGAGGATTTTGCAGATGTGATTCTGAGATTGAGAGA

TTATGCCAGATTATCCAGGTAGGCCCCAAATGTAATCACCACAGTCCTTA

TAGGAGAGGCAAGAAAGTCAAGTGTAGAAGGAGGCGATAGAAGGAGAGAG

GGATTTGAAGATTAATAGGCTGCTTGCTTTGAAGACAGAGGGAAGGGACC

ATAAACCAGAAATAAACCTCTAGAAGCTGGAAAAGGCATGGAAATAGACC

CTCCCTTAAGGTCTCTGGAGGGAGTGCAGCCTTGATTTCTACCGAGTAAA

ATTGATTTTGTACTTCAGACCTCCAAAACTGTAAGAGAATGACTGTTGTT

TTAAAACCATTGAGTTTGTAGTAATTTGTTGCAGCAGCCACAAGAAACTA

ATACAACATCTATATAGAATTTTTTCAATAATTGGAGAAATTTGAATATG

GATTGCATATTAATATTACTGAATCAGCATTAAATTTGTTAGGTGTAATA

ATGTGATTGTAGCTATTTAGGAGAATATCCTATTTTTAAGAGACATGCCA

CCATATTTAGGGAGAAGTGCCAACATATTTGCAGTTTATTTTCAAATGGT

TCAGAGGCTGTCTGTGTACATGAGAAGACAAAGATAAGGCAAATGCAGCA

AAATTGTAATAATTGGTGAATCCAGGTGAAGGGACTATGGCTGGTCTTTG

TACTTTTTTTTCCAACTTTTCTGTAGGTTTAAAATTTTCAAAATAAAAAA

ATGGGAAATACTTTAAAAATTGTAATCAAAGACATTAGTACAGAAACTTT

CATAATGTATTTTATTTTTACAGTAAAATTAATTTATGTAAATTGATAGA

ATTTTACTAATTTCACTCCCAAGTTACATTAAAAGGCTTACATATGTTTG

ATAATAGCATATGTAAACTAGAACTCTGAATGATATCCATTGGTCATAAT

-continued

ACGTACTATGTAGCGGTAATGGTGACTTTTGTGATTGCACAAGTCTAGAG

ATGCCCCAAATGACATTGACTTAGACATCTGGTTATTCTAAGGCTGAAAC

TGAAGTTGAATAGAAGGTTTTAGTCAAATACTGAGATGAAAACTGAGGCA

GTCCTGGCGGGGGGGAGTGAGTGTGTGTGTATATATACACACATAGACAT

CATGCTTCTAAACATTTACAGAAAGAAAGGGTAGATTATCTACAAAAAAA

TAAGAATCAGACTGATATGAGATCTTACAAACCTAACCCCCTTCTCTTTC

CTAAACTCCAGATTCTCATATTTCTGACTTCCTATTTGATATTTACACTT

CGATATTTACCAGGAGTCTTCAACATTTTGTTCAAAACAGTACTCTTGGT

TTTCTTCCTCCAAGACTACTCCTTACTCATATCAGCAAATAGCAGCTCTT

TTCAAGTGCTCAGTGTAAAAACCTACAATTAATCCTTGATTTCTCTTTCA

GTCAGCCTATACTAAATCAATTTCATTTAAAATATCTCGGCTACTACTCT

GCATCTCCACTGCTACCATCGGCCTCTCCAGTCACATTCTCCAAGAGCAC

TCTATCTCATTTAAAAGACAAAATCTCTGCAGTGGCCTGTGATGCTCCTT

AATGGCCTACATAATCCAGCCCTCAAGCACCTCCGTGATCTCTGTAAAAC

TTTCCCTTGGTCACTGTGCTTCAGCCACATTAACCAGCTTGCATATTTCT

CACATTCACCAAGCTTGTTCCTGCCTTGGGGCCTTTGTACTTACCATGTT

CTGTTCTGAGAATACTCTGCCTCAAGATATCCTACAACTATCTTACTGTA

TTCAGCTCTCTGCTCAAGTATTAACTGATGAAACCTGTCATCCCTACTCC

ACTCCATGTTCTGCTTTACTTAACAGCAATTGCACATATGGCCCCCTGAA

TAATATACATTTAGTCACTTATTTTTACTTATCTGCTAATTAAAATGTAG

ACTTTTTCTATTCTGTTTACTGCTGTATTCCCAGCATGTTTTATCCGAAT

GTGCAGTGGTTTCTTTTCTTCTCCCTTATCGTGGGAAGTGATGTGCACAA

ATACACATAATGGAGCCTGAATGTCATATTGCTTTCATACCTGTGTGAAT

TTTGGTAAGAAAGGAAAAGTAGCGATTGACAGGTAATATAATTACATTAA

GTCACTCTCATAGTTAGCTGTTTATTGCTTTCCTGCTCTTATTCTCAGTC

CCCAGGACCAAATGTTGACCACTACCTTCCCCCACATATAATTAGGTTAT

TTACCGAACGCCATGCAGGTGGCTGTTAAAAGGAAGATATATACTTACCT

TATAAACTCAACTTTTCCCTGTTGTCTTTCTGTCTCACCCCTACCTCCAT

GCTTTAAATTAACTTTTCAGGCTTAGGCCTTATCTCTCAGTAGAGCCATA

TAAGGTATGTGTAAAAGCAGGAAAATGTTTCCTGGGGATGAAGCTTTGAA

AAGCTTTTTTTTTTTTTCTTTTGGCAATAAAATAAGGTAGATTCAGCAC

AATACCTAATAACTAAAAAATCTGTTTTTAATTGGGTGGGGCAGACAGCA

AGTGTGTCATCCTGGAAGATACTATTTGGGATTTTATGTAGGTACATAAG

AGAAAAAAGTGAACAAAAGCAAGGGGCTACCAGGACGCCGCAGTATGCTT

AACATGTATTTTCTAAGTTTGTATTATGCCTTTATCTTGGTACTTTTATC

TTCTGTTCTCACTTGATCTTTTTGAAATGTATTTTAAATCCTAATAAAAA

TATATAAAGTCTGGAATTAATAAAGGA

Regarding the expression of lncRNA RP11-196G18.22 (LETN), it means expressions at two levels: one involves the expression at the DNA level; and the other involves the expression at the RNA level.

The term "overexpression" refers to when the strict control of gene expression (transcription) is disrupted, a gene may be inappropriately "turned off", or be transcribed at a high rate. The transcription at a high rate results in the production of a large amount of mRNA. For the overexpression of "lncRNA RP11-196G18.22" or "LETN" of the invention, it means that its DNA or RNA expression level is higher than that of the control (normal or healthy tissue/cell) by at least 30%, 40%, 50%, 60%, 70%, 80%, 90%, 100%, 110%, 120%, 130%, 140%, 150%, 200%, or 300%, or even 4, 5, 6, 7, 8, 9, 10 times or more higher than the expression level of LETN in the control.

The techniques and reagents for detecting the gene expression level are well known to those skilled in the art. In the invention, the reagent is preferably selected from a specific probe (preferably a nucleic acid probe with a detection label, usually complementary to the target gene), gene chip, or PCR primer used in the PCR specific amplification reaction for lncRNA RP11-196G18.22.

The term "reducing or inhibiting the expression of lncRNA RP11-196G18.22 (LETN)" refers to reducing the expression level of lncRNA RP11-196G18.22 (LETN) to 80% or less, 70% or less, 60% or less, 50% or less, 40% or less, 30% or less, 20% or less, 15% or less, or 10% or less, e.g., 5% or less, 2% or less, 1% or less, or even 0% of the original expression level. In one embodiment, the expression of lncRNA RP11-196G18.22 (LETN) can be reduced or inhibited by gene knockout or knockdown.

The term "knock out" refers to a genetic engineering technique in which an exogenous mutated gene is used to replace an endogenous normal homologous gene through homologous recombination, thereby inactivating the endogenous gene and exhibiting the performances of mutant.

The term "knock down" refers to the effect of preventing the gene expression by degrading the mRNA of a target gene with a homologous sequence. It efficiently and specifically degrades the homologous mRNA in cells using a double-stranded small RNA, thereby blocking the expression of the target gene in vivo and presenting the cell phenotype with target gene deletion. It prevents the gene expression by degrading the mRNA of the target gene with homologous sequence, different from the gene knockout which permanently silences the expression of the target gene.

The techniques for gene knockout or knockdown are well known in the art, and include but are not limited to the gene transfer by retrovirus and the generation of mutation, such as point mutation, insertion, deletion, frame shift, or missense mutation. Another means for gene knockout is by the use of zinc finger nuclease. The zinc finger nuclease (ZFN) is an artificial restriction enzyme produced by fusing the zinc finger DNA binding domain with the DNA cleavage domain. The zinc finger domain can be engineered to target the DNA sequence of interest, allowing the zinc finger nuclease to target the unique sequence in the complex genome. Other genome customization techniques useful for the gene knockout include TAL effector nucleases (TALEN®). Another technique involves CRISPR/Cas system for genome editing, which can be used to achieve the RNA-guided genome engineering.

The techniques to achieve "reducing or inhibiting the expression of lncRNA RP11-196G18.22 (LETN)" may also include the use of gapmer, antisense RNA, siRNA, esiRNA, shRNA, miRNA, or RNA aptamer.

"Antisense RNA" refers to an RNA molecule complementary to mRNA, and also includes RNA molecules complementary to other RNAs. Since the double-stranded RNA cannot be translated in the ribosome, the specific complementary binding of antisense RNA to mRNA inhibits the translation of the mRNA. An antisense construct can be delivered, for example, as an expression plasmid that, when expressed in a cell, produces RNA complementary to at least a unique portion of cellular lncRNA RP11-196G18.22 (LETN).

Another specific form in the antisense RNA strategy is the gapmer. The gapmer is a chimeric antisense oligonucleotide containing a central block of deoxynucleotide monomer with a sufficient length to induce the cleavage by RNase H. The design and synthesis of gapmer are well known to those skilled in the art and can be accomplished by commercial companies (e.g., Exiqon, Isis pharmaceuticals).

"Small interfering RNA (siRNA)," sometimes referred to as short interfering RNA or silencing RNA, is a class of double-stranded RNA molecules, with approximately 20-25 base pairs in length, that function by the way of RNA interference (RNAi). It interferes with the expression of mRNA post-transcriptionally degraded for the specific gene with complementary nucleotide sequence, thereby preventing translation. The siRNA of the invention can target any segment of about 19 to 25 continuous nucleotides in the lncRNA RP11-196G18.22 (LETN) target sequence, examples of which are provided in this application. The techniques for selecting the target sequence for siRNAs are well known in the art.

"Short hairpin RNA" (abbreviated as shRNA) is an RNA sequence comprising two short inverted repeat sequences that can silence the gene expression via RNA interference (RNAi).

The full English name of "esiRNA" is endoribonuclease-prepared siRNA. It is a mixture of siRNAs generated by cleaving long double-stranded RNAs (dsRNAs) by RNase III (ribonuclease) of *E. coli*, with a length of 18-25 bp, and can be used to efficiently knock down the expression level of the target gene.

The invention is based on the unexpected finding that lncRNA RP11-196G18.22 (LETN) can be used as a tumor marker and a therapeutic target. Thus, the invention provides the use of an agent for detecting the expression level of lncRNA RP11-196G18.22 (LETN) in the manufacture of a diagnostic agent or a diagnostic kit for cancer. The invention also provides the use of an agent for reducing or inhibiting the expression of lncRNA RP11-196G18.22 (LETN) in the manufacture of a medicament for treating cancer. In addition, the invention also provides a method for screening anticancer drugs, comprising the step of determining whether the candidate compound can reduce or inhibit the expression of lncRNA RP11-196G18.22 (LETN).

The invention is further illustrated in Examples below. These Examples are for illustrative purposes only and are not intended to limit the scope of the invention. The chemicals used in the reactions below are all commercially available products, unless otherwise indicated.

The unpaired student's t-test is used for statistical analysis in the invention. Statistical calculations are performed using Microsoft Excel. When $P<0.05$, P value is significant.

Example 1 Screening of lncRNA RP11-196G18.22 (LETN)

Figure 1:
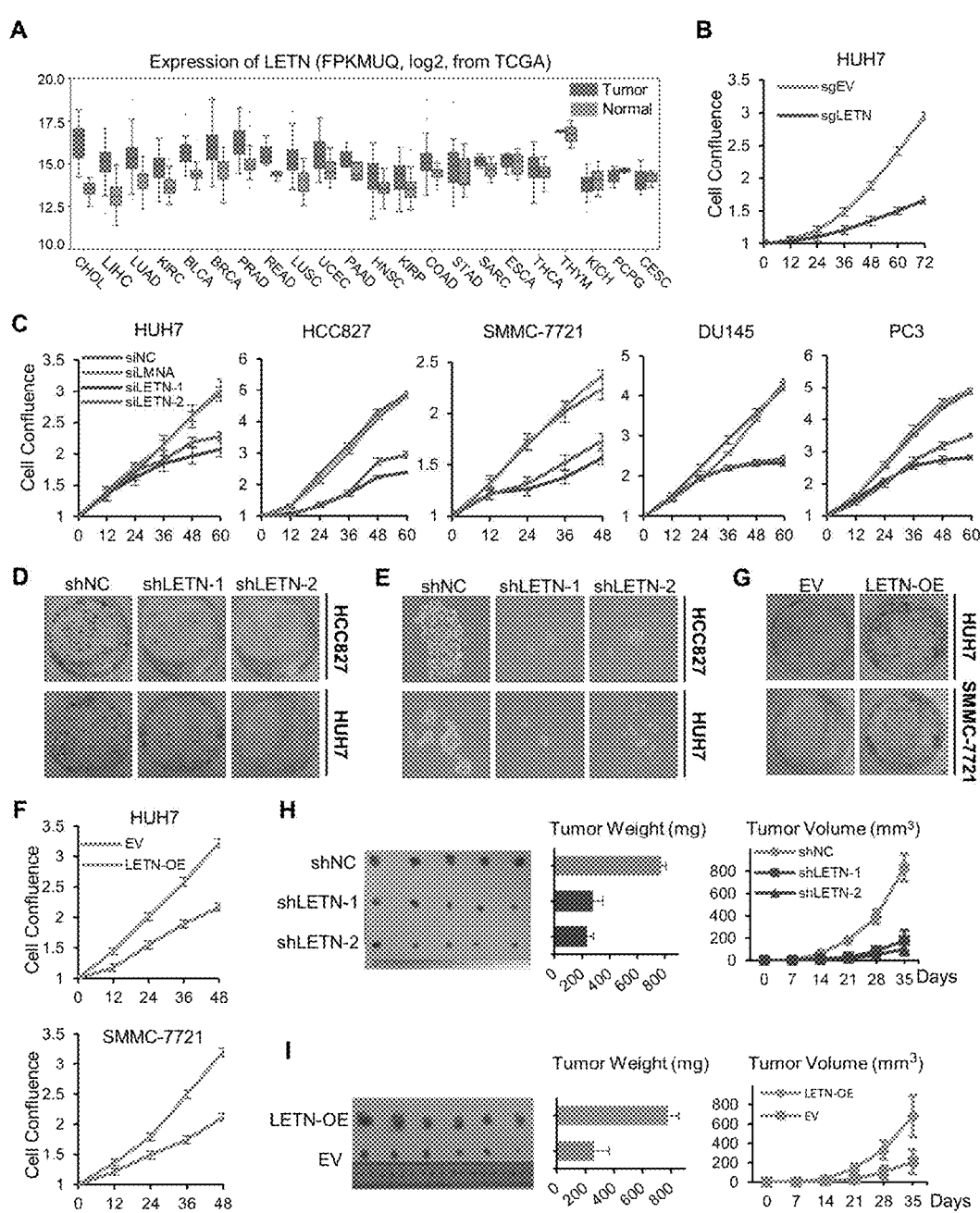
FIG. 1 The results shown in A to J in FIG. 1 show that LETN can promote the carcinogenesis and progress of liver hepatocellular carcinoma.

For the liver hepatocellular carcinoma (LIHC), lncRNA functions were investigated using the data of the Cancer Genome Atlas (TCGA), to predict lncRNAs with the functions of regulating transcription factors and their target genes through an algorithm designed in the laboratory. Through the comprehensive screening based on three factors: the regulation logarithm, the presence or absence of a difference in expression between cancer and paracancerous tissue, and the variation in genome copy number, 22 lncR- NAs were finally selected (UBE2SP2, BMS1P8, RP11-443P15.2, LINC01296/DUXAP10, LL22NC03-N14H11.1, RP11-284F21.10, DUXAP8, CRNDE, CTD-2227E11.1, LINC00853, LINC00665, RP11-196G18.22, GOLGA2P7, RP11-14N7.2, PVT1, LINC00511, RP11-396C23.2, MIR4435-2HG, AL450992.2, HCG25, PCAT6, LINC00152). After removing several lncRNAs with non-specific sequences (the sequences are completely located in the exon of a gene, and specific siRNAs cannot be designed for functional verification), there remained 16 lncRNAs, and then the phenotypes of these lncRNAs were verified through experiments. Specifically, siRNAs specific for its transcript were designed (see Table 1 below), and the liver hepatocellular carcinoma cell line HUH7 (Shanghai Cell Bank, Chinese Academy of Sciences) was transfected by liposome LIPOFECTAMINE® 2000 (Thermo Fisher, 11668019), to detect the effect of the knockdown of corresponding lncRNA on the cell proliferation. It was found that (see FIG. 5), only seven lncRNAs (DUXAP8, PCAT6, LINC00511, LINC00152, RP11-198G18.22, PVT1, and CRNDE, 7 lncR-NAs on the right in FIG. 5) could inhibit the proliferation of HUH7 cells, while only one of these seven lncRNAs, namely lncRNA RP11-196G18.22 (designated as LETN), had not been reported so far. It was also a lncRNA having the largest numbers of regulated transcription factors and target genes as previously found in the algorithm prediction, suggesting that it may have extensive and powerful regulatory potentials in the carcinogenesis and progress of liver hepatocellular carcinoma. Based on the above findings, the expression levels of LETN were analyzed in liver hepatocellular carcinoma and paracancerous tissues in the TCGA database, and it was found that the expression level of LETN in the liver hepatocellular carcinoma tissue was much higher than those in paracancerous tissues; and it was further found in extended analyses on other cancer tissues that, the expression levels of LETN in most cancers were all higher than those in paracancerous tissues (FIG. 1, A).

TABLE 1

| siRNA | Sense 5'-3' | Antisense 5'-3' |
| --- | --- | --- |
| siRP11-284F21.10 | CCAGUUCUCCUAAA UGCUU (SEQ ID NO: 2) | AAGCAUUUAGGAGAACUGG (SEQ ID NO: 3) |
| siLL22NC03-N14H11.1 | GAGCCUUUCCUGCC CGCUU (SEQ ID NO: 4) | AAGCGGGCAGGAAAGGCUC (SEQ ID NO: 5) |
| siLINC00853 | GCUCUCAUCAAUCU ACGCU (SEQ ID NO: 6) | AGCGUAGAUUGAUGAGAGC (SEQ ID NO: 7) |
| siCTD-2227E11.1 | GUGUCUCUGGGAAG CCCUU (SEQ ID NO: 8) | AAGGGCUUCCCAGAGACAC (SEQ ID NO: 9) |
| siAL450992.2 | GGAGUCAUGUGUUG GAGAU (SEQ ID NO: 10) | AUCUCCAACACAUGACUCC (SEQ ID NO: 11) |
| siRP11-14N7.2 | CUCCACAUAUGAAAC CCUU (SEQ ID NO: 12) | AAGGGUUUCAUAUGUGGAG (SEQ ID NO: 13) |
| siLINC00665 | CAGAUGAAGGUAUAU CAUU (SEQ ID NO: 14) | AAUGAUAUACCUUCAUCUG (SEQ ID NO: 15) |

TABLE 1-continued

| siRNA | Sense 5'-3' | Antisense 5'-3' |
| --- | --- | --- |
| siRP11-396C23.2 | GCCGUCGCCGCAGCU CCUU (SEQ ID NO: 16) | AAGGAGCUGCGGCGACGGC (SEQ ID NO: 17) |
| siHCG25 | CCACUCUCAGCCUCA GGAA (SEQ ID NO: 18) | UUCCUGAGGCUGAGAGUGG (SEQ ID NO: 19) |
| siDUXAP8 | CCUGGUAAGGCUUGA AGUU (SEQ ID NO: 20) | AACUUCAAGCCUUACCAGG (SEQ ID NO: 21) |
| siPCAT6 | CUCCAAUUCAAUGCC AUCA (SEQ ID NO: 22) | UGAUGGCAUUGAAUUGGAG (SEQ ID NO: 23) |
| siLINC00511 | CUCCCAGAAUGCCAG GAUU (SEQ ID NO: 24) | AAUCCUGGCAUUCUGGGAG (SEQ ID NO: 25) |
| siLINC00152 | CCGUCUGCAUCCCUC GAAU (SEQ ID NO: 26) | AUUCGAGGGAUGCAGACGG (SEQ ID NO: 27) |
| siRP11-196G18.22 | GCUGUCUCCAUGUCU UCUU (SEQ ID NO: 28) | AAGAAGACAUGGAGACAGC (SEQ ID NO: 29) |
| siPVT1 | GGACUUGAGAACUGU CCUU (SEQ ID NO: 30) | AAGGACAGUUCUCAAGUCC (SEQ ID NO: 31) |
| siCRNDE | UGUUGAAAUGAAAAA UAUU (SEQ ID NO: 32) | AAUAUUUUUCAUUUCAACA (SEQ ID NO: 33) |

Example 2 Study of lncRNA RP11-196G18.22 (LETN) on the Cellular Level

Two liver hepatocellular carcinoma cell lines were selected, namely HUH7 (Shanghai Cell Bank, Chinese Academy of Sciences) and SMMC-7721 (Shanghai Cell Bank, Chinese Academy of Sciences), and LETN was knocked down by siRNA (siRNA primers are shown below). The cells were seeded in a 35 mm dish for transfection after cell adherence. 2 μl of liposome LIPOFECTAMINE® 2000 (Thermo Fisher, 11668019) and 20 nM of siRNA were diluted with 250 ml of medium, respectively. After mixing well, the mixture was incubated for 20 min on standing, then slowly dropped into the dish containing the cells, and the knockdown level was detected by RT-qPCR after 48 hours (see Table 2 below for the sequence of primer pairs). The knockdown efficiency is shown in FIG. 4A. It is found that LETN knockdown can significantly reduce the proliferation of cells (FIG. 1, C) (siNC and siLMNA are two different negative controls; to prevent off-target effects, two siRNAs are designed for LETN knockdown: siLETN-1 and siLETN-2).

siLETN-1
Sense
(SEQ ID NO: 34)
5'-3' GCUGUCUCCAUGUCUUCUU

Antisense
(SEQ ID NO: 35)
5'-3' AAGAAGACAUGGAGACAGC

-continued siLETN-2
Sense
(SEQ ID NO: 36)
5'-3' GCUCUCUGCUCAAGUAUUA

Antisense
(SEQ ID NO: 37)
5'-3' UAAUACUUGAGCAGAGAGC siNC(negative control)
Sense
(SEQ ID NO: 38)
5'-3' ACGUGACACGUUCGGAGAA Antisense
(SEQ ID NO: 39)
5'-3' UUCUCCGAACGUGUCACGU siLMNA
Sense
(SEQ ID NO: 40)
5'-3' AUCUCAUCCUGAAGUUGCUUC Antisense
(SEQ ID NO: 41)
5'-3' GAAGCAACUUCAGGAUGAGAU

TABLE 2

| Gene ID | forward primer 5'-3' | reverse primer 5'-3' |
|---|---|---|
| LETN-1 | GGGTCTACCTGTGAACTGTGA (SEQ ID NO: 42) | GGAAACACATGTGGCAGCAC (SEQ ID NO: 43) |
| LETN-2 | TGGTTTCTGGCAGCATAACT (SEQ ID NO: 44) | AGCCTGGGCAACAAGAGTGA (SEQ ID NO: 45) |
| NPM1-N | TTCGGTTGTGAACTAAAGGC (SEQ ID NO: 46) | CAAGGGAAACCGTTGGCTGT (SEQ ID NO: 47) |
| NPM1-C | TCTGTAGAAGACATTAAAGCAAA (SEQ ID NO: 48) | AATAGCCTCTTGGTCAGTCAT (SEQ ID NO: 49) |
| Pre-rRNA | GCCTTCTCTAGCGATCTGAGAG (SEQ ID NO: 50) | CCATAACGGAGGCAGAGACA (SEQ ID NO: 51) |
| 18S rRNA | TCCTTTGGTCGCTCGCTCCT (SEQ ID NO: 52) | GATCTGATAAATGCACGCATCCC (SEQ ID NO: 53) |
| 5.8S rRNA | ACTCGGCTCGTGCGTC (SEQ ID NO: 54) | GCGACGCTCAGACAGG (SEQ ID NO: 55) |
| 28S rRNA | GCGGGTAAACGGCGGGAGTA (SEQ ID NO: 56) | TTGGCTGTGGTTTCGCTGGAT (SEQ ID NO: 57) |
| GAPDH | GGTCACCAGGGCTGCTTTTA (SEQ ID NO: 58) | TTCCCGTTCTCAGCCTTGAC (SEQ ID NO: 59) |
| β-actin | TGGACATCCGCAAAGACCTG (SEQ ID NO: 60) | CCGATCCACACGGAGTACTT (SEQ ID NO: 61) |
| MALAT1 | GCTCTGTGGTGTGGGATTGA (SEQ ID NO: 62) | GTGGCAAAATGGCGGACTTT (SEQ ID NO: 63) |

Since two weeks of continuous knockdown was required to detect the colony formation, a stably screened cell line with LETN knockdown was constructed (see Example 3 for details). The knockdown level was detected by RT-qPCR (see Table 3 below for the sequence of primer pairs). The knockdown efficiency was shown in FIG. 4B. It was found that the knockdown of LETN could significantly reduce the colony formation of cells (FIG. 1, D, E). The shNC was the negative control group.

TABLE 3

| shRNA | Sense 5'-3' | Antisense 5'-3' |
|---|---|---|
| shLETN-1 | GGACTTCCAGTTAAGCCAATT (SEQ ID NO: 64) | AATTGGCTTAACTGGAAGTCC (SEQ ID NO: 65) |
| shLETN-2 | GGCTGTCTCCATGTCTTCTTA (SEQ ID NO: 66) | TAAGAAGACATGGAGACAGCC (SEQ ID NO: 67) |
| shNC | ACGTGACACGTTCGGAGAAA (SEQ ID NO: 68) | TTTCTCCGAACGTGTCACGT (SEQ ID NO: 69) |

In addition, LETN was knocked out by CRISPR-Cas9. The cells were seeded in a 35 mm dish for transfection after cell adherence. 2 μl of liposome LIPOFECTAMINE® 2000 (Thermo Fisher, 11668019) and 2 μg of px458-sgRNA plasmid (sgLETN sequence was added on the basis of px458 (Addgene, catalog no. 48138), and the specific method is shown in the reference [5]) were diluted with 250 ml of medium, respectively. After mixing well, the mixture was incubated for 20 min on standing, then slowly dropped into the dish containing the cells, and the knockdown level was detected by RT-qPCR after 48 hours. The knockdown efficiency is shown in FIG. 4C. It was found that the proliferation of cells was significantly inhibited (FIG. 1, B).

sgLETN-1
Sense
(SEQ ID NO: 70)
5'-3' TCAAATTTCAGTCGGAACTC sgLETN-2
Sense
(SEQ ID NO: 71)
5'-3' GAGACGATATGCTACGGGTG sgEV-1
Sense
(SEQ ID NO: 72)
5'-3' GAACGTTGGCACTACTTCAC sgEV-2
Sense
(SEQ ID NO: 73)
5'-3' GCGCCTTAAGAGTACTCATC On the other hand, LETN overexpression was performed. The cells were seeded in a 35 mm dish for transfection after cell adherence. 2 μl of liposome LIPOFECTAMINE® 2000 (Thermo Fisher, 11668019) and 2 μg of LETN overexpression plasmid plv-LETN (constructed by Wuxi Qinglan Biotechnology Co., Ltd., the expression plasmid: plv-mCherry, catalog no. 36084) were diluted with 250 ml of medium, respectively. After mixing well, the mixture was incubated for 20 min on standing, then slowly dropped into the dish containing the cells, and the overexpression efficiency was detected by RT-qPCR after 48 hours (see FIG. 4, D). It was found that the proliferation and colony formation of cells could be promoted (FIG. 1, F, G).

Subsequently, the lung cancer cell line HCC827 (ATCCRCRL-2868) as well as the prostate cancer cell lines DU145 (ATCCRHTB-81) and PC3 (ATCCRCRL-1435) were selected, and similar effects were found. When LETN was knocked down by siRNA (the method is identical to that previously manipulated in the liver hepatocellular carcinoma cell line HUH7, and the knockdown efficiency is shown in FIG. 4A), the proliferation rate of cells was significantly reduced, and the colony formation ability was also destroyed (FIG. 1, C).

Example 3 Study of lncRNA RP11-196G18.22 (LETN) on Animal Level

The effect of LETN on the tumorigenic ability of tumor cells was further investigated. Firstly, a stably screened cell line with LETN knockdown was constructed using the virus packaging shRNA (shRNA sequences are shown in Table 3). First, for virus packaging, 293T cells (Shanghai Cell Bank, Chinese Academy of Sciences) were seeded in a 100 mm plate, and transfected on the next day. 12 µl of liposome LIPOFECTAMINE® 2000 (Thermo Fisher, 11668019) was diluted with 1 ml of medium, and the packaging vector 7.1 µl Δ8.9 (Tsinghua University library platform), 3.55 µg VSVG (Tsinghua University library platform), and the expression vector 3 µg plv-LETN were diluted with 1 ml of medium. After mixing well, the mixture was incubated for 20 min on standing, then slowly dropped into the dish containing the cells, and the medium was supplemented to 10 ml. After 48 hours, the supernatant was collected and centrifuged at 3000 rpm for 10 min. This supernatant as the virus solution was aliquoted, and stored at −80° C. until use. For the construction of the stably screened cell line with LETN knockdown, first, the cells were seeded in a 35 mm dish, 500 µl of virus solution was added on the next day, and the medium was supplemented to 2 ml. After 48 hours, puromycin was added once every three days to remove cells without viral expression, to obtain the stably screened cell line as desired). The HUH7 cell line with LETN knockdown (the knockdown efficiency was detected by RT-qPCR, and shown in FIG. 4B) was subcutaneously injected into athymic nude mice (BALB/c nude mice, male, from the Animal Center of Tsinghua University). After inoculation for 5 weeks, the size of tumor mass was measured weekly with vernier caliper. The tumor was removed to measure its weight and volume. It was found that the tumor mass formed by the cells with LETN knockdown was significantly smaller than the control group, and the tumor volume and weight were much smaller than those of the control group (FIG. 1, H). Accordingly, HUH7 was selected to construct a stably screened cell line with LETN overexpression, which was subcutaneously injected into athymic nude mice. After inoculation for 5 weeks, the same operations were performed. It was found that the tumor mass formed by the cells with LETN overexpression was significantly larger than the control group, and the tumor volume and weight were much larger than those of the control group (FIG. 1, I). In sum, by detailed experimental verifications on basis of tumor indicators such as cell proliferation, colony formation, and subcutaneous tumorigenesis, it was believed that lncRNA LETN has a significant function of inhibiting the carcinogenesis and progress of liver hepatocellular carcinoma and is a potential therapeutic target.

Example 4 Exploration of Action Mechanism of LETN

First, it was identified by RNA in situ hybrization[6] and nucleocytoplasmic separation (Nuclear/Cytosol Fractionation Kit (Biovision, K266-25)) that LETN was mainly localized in the nucleus and distributed in clusters. This indicated that LETN was likely to function through binding to proteins. The proteins pulled down through RNA pull down were analyzed by mass spectrometry to find the proteins that interact with LETN, and finally NPM1 was found to be the functional protein that binds thereto. Then NPM1 antibody Anti-NPM1 (Abcam, ab10530) was used for pulling down through RNA pull down technology[7], and it was also found that NPM1 could indeed pull down lncRNA LETN. It was further confirmed by the cellular fluorescence co-localization experiment that LETN was localized in the nucleolus.

NPM1 is a very crucial functional protein in the nucleolus, which can bind to rDNA promoter to promote rDNA transcription; participate in rRNA splicing and maturation; bind to histones and participate in nucleosome assembly; and the like. It was found that LETN was indeed involved in these functions. It was found that the knockdown of LETN could significantly reduce the expressions of various rRNAs, and the overexpression of LETN could promote the expression of rRNA. In addition, the knockdown of LETN could also attenuate the binding ability of NPM1 to histones, thereby affecting the nucleosome assembly. The nucleolus is composed of three basic structural components, namely fibrillar center, dense fibrillar component, and granular component (from the inside to the outside). NPM1 is mainly located in the outermost layer and is the most important constituent of the granular component. Studies have shown that the knockdown of NPM1 can destroy the morphology of the nucleolus.

Our study found that when LETN was knocked down, the nucleolus became irregular and scattered from the regular and dense spherical shape, indicating that LETN also affected the structure of the nucleolus. Through our algorithm, the survival time was analyzed based on the clinical data of liver hepatocellular carcinoma patients in the TCGA database, wherein these groups were individually divided: LETN high expression group and low expression group, or NPM1 high expression group and low expression group. It was found that the prognostic survival time of patients in NPM1 or LETN high expression group was shorter than that of patients in low expression group; and when further subdivided into four groups: NPM1-low+LETN-low, NPM1-low+LETN-high, NPM1-high+LETN-low, and NPM1-high+LETN-high, it was found that the survival time of patients with high expressions of both NPM1 and LETN was much shorter than that of patients with low expressions of both NPM1 and LETN.

Those skilled in the art should understand that, although the invention is described in details with reference to the above Examples, the invention is not limited to these specific Examples. Based on the methods and technical solutions taught by the invention, those skilled in the art can make appropriate modifications or improvements without departing from the spirit of the invention, and the equivalent embodiments thus obtained are all within the scope of the invention.

REFERENCES

1. Schmitt A M, Chang H Y: Long Noncoding RNAs in Cancer Pathways. *Cancer Cell* 2016, 29(4):452-463.
2. Bray F, Ferlay J, Soerjomataram I, Siegel R L, Torre L A, Jemal A: Global cancer statistics 2018: GLOBOCAN estimates of incidence and mortality worldwide for 36 cancers in 185 countries. *CA: A Cancer Journal for Clinicians* 2018, 68(6):394-424.

3. Scudellari M: Drug development: Try and try again. *Nature* 2014, 516:S4.
4. Box J K, Paquet N, Adams M N, Boucher D, Bolderson E, O'Byme K J, Richard D J: Nucleophosmin: from structure and function to disease development. *BMC Mol Biol* 2016, 17(1):19.
5. Ran F A, Hsu P D, Wright J, Agarwala V, Scott D A, Zhang F: Genome engineering using the CRISPR-Cas9 system. *Nat Protoc* 2013, 8(11):2281-2308.
6. Kawaguchi T, Tanigawa A, Naganuma T, Ohkawa Y, Souquere S, Pierron G, Hirose T: SWI/SNF chromatin-remodeling complexes function in noncoding RNA-dependent assembly of nuclear bodies. *Proceedings of the National Academy of Sciences of the United States of America* 2015, 112(14):4304-4309.

7. Li X, Wang X, Song W, Xu H, Huang R, Wang Y, Zhao W, Xiao Z, Yang X: Oncogenic Properties of NEAT1 in Prostate Cancer Cells Depend on the CDC5L-AGRN Transcriptional Regulation Circuit. *Cancer Res* 2018, 78(15):4138-4149.

What is claimed is:

1. A method for treating cancer, the method comprising administrating to a subject in need thereof an effective amount of an agent for reducing or inhibiting the expression of lncRNA RP11-196G18.22 (LETN), wherein the cancer is a solid tumor selected from the group consisting of liver hepatocellular carcinoma, lung cancer, and prostate cancer.

2. The method according to claim 1, wherein the agent for reducing or inhibiting the expression of lncRNA RP11-196G18.22 (LETN) is selected from the group consisting of gapmer, antisense RNA, siRNA, esiRNA, shRNA, miRNA, RNA aptamer, transcription activator-like effector nuclease, CRISPR, and zinc finger nuclease.

3. The method according to claim 1, wherein the lncRNA RP11-196G18.22 has the nucleotide sequence as shown in SEQ ID NO: 1 (Ensembl accession number: ENST00000564237.1).

4. The method according to claim 1, wherein the method further comprises administrating to the subject an additional anticancer agent, wherein the additional anticancer agent comprises a chemotherapeutic agent.

* * * * *